(12) United States Patent
Balazs et al.

(10) Patent No.: US 10,383,890 B2
(45) Date of Patent: *Aug. 20, 2019

(54) COMPOSITIONS OF HYALURONAN WITH HIGH ELASTICITY AND USES THEREOF

(71) Applicant: Matrix Biology Institute, Edgewater, NJ (US)

(72) Inventors: Endre A. Balazs; Carlos Belmonte, San Juan De Alicante (ES)

(73) Assignee: Matrix Biology Institute, Edgewater, NJ (US)

( * ) Notice: Subject to any disclaimer, the term of this patent is extended or adjusted under 35 U.S.C. 154(b) by 129 days.

This patent is subject to a terminal disclaimer.

(21) Appl. No.: 15/290,107

(22) Filed: Oct. 11, 2016

(65) Prior Publication Data

US 2017/0071974 A1    Mar. 16, 2017

Related U.S. Application Data

(63) Continuation of application No. 14/327,321, filed on Jul. 9, 2014, now Pat. No. 9,492,474.

(60) Provisional application No. 61/844,645, filed on Jul. 10, 2013.

(51) Int. Cl.
| | | |
|---|---|---|
| A61K 47/02 | (2006.01) | |
| A61K 31/728 | (2006.01) | |
| C08B 37/08 | (2006.01) | |
| A61K 9/00 | (2006.01) | |

(52) U.S. Cl.
CPC .......... *A61K 31/728* (2013.01); *A61K 9/0019* (2013.01); *A61K 47/02* (2013.01); *C08B 37/0072* (2013.01)

(58) Field of Classification Search
CPC .......................... A61K 31/728; C08B 37/0072
See application file for complete search history.

(56) References Cited

U.S. PATENT DOCUMENTS

| | | | |
|---|---|---|---|
| 4,141,973 A | 2/1979 | Balazs | |
| 6,953,776 B2 | 10/2005 | Di Napoli | |
| 7,544,671 B2 | 6/2009 | Karageozian et al. | |
| 7,674,781 B2 | 3/2010 | Sheardown et al. | |
| 7,863,256 B2 | 1/2011 | Schiavinato et al. | |
| 7,943,596 B2 | 5/2011 | Ueno et al. | |
| 8,093,365 B2 | 1/2012 | Wisniewski et al. | |
| 8,153,614 B2 | 4/2012 | Asari | |
| 8,323,617 B2 | 12/2012 | Gooding et al. | |
| 8,329,746 B2 | 12/2012 | Waddell | |
| 8,338,388 B2 | 12/2012 | Lebreton | |
| 8,388,995 B1 | 3/2013 | Ali et al. | |
| 8,398,611 B2 | 3/2013 | Hwang et al. | |
| 8,455,436 B2 | 6/2013 | Byers et al. | |
| 8,524,662 B2 | 9/2013 | Byers et al. | |
| 8,529,938 B2 | 9/2013 | Jafari et al. | |
| 8,563,532 B2 | 10/2013 | Lebreton | |
| 9,044,425 B2 | 6/2015 | Babizhayev | |
| 9,492,474 B2 | 11/2016 | Balazs et al. | |
| 2004/0167480 A1 | 8/2004 | Bos | |
| 2006/0094643 A1 | 5/2006 | Svirkin et al. | |
| 2007/0293648 A1 | 12/2007 | Sheardown et al. | |
| 2008/0050335 A1 | 2/2008 | Faour et al. | |
| 2010/0048755 A1 | 2/2010 | Chow et al. | |
| 2010/0074957 A1 | 3/2010 | Robinson et al. | |
| 2010/0178317 A1 | 7/2010 | Burke et al. | |
| 2010/0184720 A1 | 7/2010 | Gavard Molliard et al. | |
| 2010/0303915 A1 | 12/2010 | Yu | |
| 2011/0066138 A1 | 3/2011 | Fezza | |
| 2012/0128754 A1 | 5/2012 | Wei | |
| 2012/0165257 A1* | 6/2012 | Byers ................. | A61K 38/1875 514/8.8 |
| 2012/0258931 A1 | 10/2012 | Bailleul | |
| 2013/0195952 A1 | 8/2013 | Byrne et al. | |
| 2013/0209531 A1 | 8/2013 | Prestwich et al. | |
| 2013/0296264 A1 | 11/2013 | Davis et al. | |
| 2013/0303695 A1 | 11/2013 | Sheardown et al. | |
| 2014/0221309 A1 | 8/2014 | Beard et al. | |
| 2015/0018305 A1 | 1/2015 | Asari et al. | |
| 2015/0037422 A1 | 2/2015 | Kaplan et al. | |
| 2015/0148310 A1 | 5/2015 | Prestwich | |
| 2015/0151858 A1 | 6/2015 | Turzi | |
| 2015/0173951 A1 | 6/2015 | Fezza | |
| 2015/0209385 A1 | 7/2015 | Prestwich et al. | |
| 2017/0071974 A1 | 3/2017 | Balazs et al. | |

FOREIGN PATENT DOCUMENTS

| | | |
|---|---|---|
| EP | 0414373 A2 | 2/1991 |
| EP | 1908457 A1 | 4/2008 |
| EP | 2596796 A1 | 5/2013 |
| EP | 2614838 A1 | 7/2013 |
| EP | 2979539 A1 | 2/2016 |
| WO | WO-1998/39015 A1 | 9/1998 |
| WO | WO-2011/044367 A1 | 4/2011 |
| WO | WO-2012/143876 A1 | 10/2012 |
| WO | WO-2013/186493 A2 | 12/2013 |
| WO | WO-2014/032804 A1 | 3/2014 |
| WO | WO-2014/152328 A1 | 9/2014 |

(Continued)

OTHER PUBLICATIONS

Mo, Y. et al "Effects of sodium chloride . . . " Biopolymers, vol. 50, pp. 23-34 (Year: 1999).*

(Continued)

*Primary Examiner* — Leigh C Maier

(74) *Attorney, Agent, or Firm* — McCarter & English, LLP; Maria Laccotripe Zacharakis

(57) ABSTRACT

The present invention provides compositions comprising hyaluronan with high elasticity, as well as methods for improving joint function, reducing pain associated with joint function and treating osteoarthritis by introducing into a joint a therapeutically effective amount of a composition comprising hyaluronan with high elasticity.

28 Claims, 15 Drawing Sheets

(56) References Cited

FOREIGN PATENT DOCUMENTS

| WO | WO-2014/156939 A1 | 10/2014 |
|---|---|---|
| WO | WO-2014/191955 A1 | 12/2014 |
| WO | WO-2015/097261 A1 | 7/2015 |

OTHER PUBLICATIONS

[No Author Listed], "Design and Conduct of Clinical Trials: Report of the Clinical Trials Subcommittee of the International Dry Eye Workshop (2007)," The Ocular Surface, vol. 5, No. 2, pp. 153-162, 2007.

[No Author Listed], "Management and Therapy of Dry Eye Disease: Report of the Management and Therapy Subcommittee of the Intenational Dry Eye Workshop (2007)," The Ocular Surface, vol. 5, No. 2, pp. 163-178, 2007.

[No Author Listed], "Methodologies to Diagnose and Monitor Dry Eye Disease: Report of the Diagnostic Methodology Subcommittee of the International Dry Eye Workshop (2007)," The Ocular Surface, vol. 5, No. 2, pp. 108-152, 2007.

[No Author Listed], "Research in Dry Eye: Report of the Research Subcommittee of the International Dry Eye Workshop (2007)," The Ocular Surface, vol. 5, No. 2, pp. 179-193, 2007.

[No Author Listed], "Sodium Hyaluronate Ophthalmic Solution 0.18% for the Treatment of the Signs and Symptoms of Dry Eye Disease," Dermatologic and Ophthalmic Drugs Advisory Committee Meeting Briefing Document, NDA 22-359 FDA Advisory Committee Briefing Document, pp. 1-115, 2009.

[No Author Listed], "The Definition and Classification of Dry Eye Disease: Report of the Definition and Classification Subcommitte of the International Dry Eye Workshop (2007)," The Ocular Surface, vol. 5, No. 2, pp. 75-92, 2007.

[No Author Listed], "The Epidemiology of Dry Eye Disease: Report of the Epidemiology Subcommittee of the International Dry Eye Workshop (2007)," The Ocular Surface, vol. 5, No. 2, pp. 93-107, 2007.

Acosta M. C. et al., "Sensory experiences in humans and single-unit activity in cats evoked by polymodal stimulation of the cornea," Journal of Physiology, vol. 534.2, pp. 511-525, 2001.

Acosta, M. C. et al., "Corneal Sensory Nerve Activity in an Experimental Model of UV Keratitis," IOVS, vol. 55, No. 6, pp. 3403-3412, 2014.

Acosta, M. C. et al., "The Influence of Eye Solutions on Blinking and Ocular Comfort at Rest and During Work at Video Display Terminals," Experiemental Eye Research, vol. 68, No. 6, pp. 663-669, 1999.

Alves, M. et al., "Dry Eye Disease Treatment: A Systematic Review of Published Trials and a Critical Appraisal of Therapeutic Strategies," The Ocular Service, vol. 11, No. 3, pp. 181-192, 2013.

Aragona P. et al., "Long term treatment with sodium hyaluronate-containing artifical tears reduces ocular surface damage in patients with dry eye," Br J Ophthalmol, vol. 86, pp. 181-184, 2002.

Aragona P. et al., "Sodium hyaluronate eye drops of different osmolarity for the treatment of dry eye in Sjögren's syndrome patients," Br J Ophthalmol, vol. 86, pp. 879-884, 2002.

Arshinoff S. A. et al., "HsS versus a balanced salt solution as a corneal wetting agent during routine cataract extraction and lens implantation," J Cataract Refract Surg, vol. 23, pp. 1221-1225, 1997.

Balazs et al., Viscosupplementation: a new concept in the treatment of osteoarthritis, The Journal of Rheumatology (1993), Suppl; 39, 20:3-9.

Balazs, E.A., "Viscosupplementation for the Treatment of Osteoarthritis: From Initial Discovery to Current Status and Results." A Reprint from Surgical Technology International XII, Ed. By Z. Szabo, A. J. Coburg, P. S. Strange, J. E. Lewis and R. S. Savalgi.

Belmonte, C. et al., "Modulation by hyaluronan and its derivatives (hylans) of sensory nerve activity signalling articular pain." In the Chemistry, Biology and Medical Applications of Hyaluronan and its Derivatives Proceedings of the Wenner-Gren Foundation International Symposium, held in honor of Endre A Balazs, Stockholm, Sweden, Sep. 18-21, 1996. (Ed. Laurent, T. C.), Portland Press Ltd., London, 205-217.

Berenbaum, F. et al., "A randomised, double-blind, controlled trial comparing two intra-articular hyaluronic acid preprations differing by their molecular weight in symptomatic knee osteoarthritis," Ann Rheum Dis, vol. 71, pp. 1454-1460, 2012.

Biomatrix, Inc., "Hylashield® CL Lubricating Eye Drop hylan fluid, 0.15% Lubricant—Wetting/Rewetting Drop," 8 pages, 2000.

Boettger, M. et al., "Evaluation of long-term antinociceptive properties of stabilized hyaluronic acid preparation (NASHA) in an animal model of repetitive joint pain." Arthritis Research and Therapy (Open Access), 2011, 13: R1110. http://arthritis-research.com/content/13/4/R110.

Borzacchiello, A. et al., "Effect of hyaluronic acid amide derivative on equine synovial fluid viscoelasticity." Wiley Periodicals Inc., J. Biomed. Mater. Res., 2010, 92A: 1162-1170.

Bothner, H. and Wik, O., "Rheology of Hyaluronate" Acta Otolaryngol , Stockholm, vol. 104, Suppl. 442: 25-30 (1987).

Bron A. J. et al., "Rethinking Dry Eye Disease: A Perspective on Clinical Implications," The Ocular Surface, vol. 12, No. 2S, pp. S1-S31, 2014.

Cheema A. et al., "Sodium hyaluronate eye drops in the treatment of dry eye disease: an open label, uncontrolled, multi-centre trial," J. Ayub. Med. Coll. Abbottabad, vol. 24, pp. 14-16, 2012.

Colligris, B. et al., "Recent Developments on dry eye disease treatment compounds," Saudi Journal of Ophthalmology, vol. 28, pp. 19-30, 2014.

Cowman, M et al., "Experimental approaches to hyaluronan structure." Carbohydrate Research (2005), 340: 791-809.

Cowman, M.K., "Macromolecular Crowding in the Biomatrix", in Structure and Function of Biomatrix: Control of Cell Behavior and Gene Expression, E.A. Balazs, ed., Matrix Biology Institute, Edgewater, NJ, (2012), pp. 45-66.

Craig, Jennifer, P., "Dry Eye Part 2: Current therapeutic and management options," Bausch & Lomb Academy of Vision Care, 11 pages, 2009.

De Smedt, S. C. et al., "Viscoelastic and transient network properties of hyaluronic acid as a function of the concentration." Biorheology, (1993) 30:31-41.De Smedt et al., "Viscoelastic and transient network properties of hyaluronic acid as a function of the concentration." Biorheology, (1993) 30:31-41.

DeLuise V. P. et al., "The Use of Topical Healon Tears in the Management of Refractory Dry-Eye Syndrome," Annals of Ophthalmology, pp. 823-824, 1984.

Dumbleton K. et al., "An Investigation of th Efficacy of a Novel Ocular Lubricant," Eye & Contact Lens, vol. 35, No. 3, pp. 149-155, 2009.

Falcone, S. J. et al., "Rheological and cohesive properties of hyaluronic acid." J. Biomed. Mater. Res., (2006), 76A : 721-728.

Fam, H. et al., "Effect of concentration and molecular weight on the rheology of hyaluronic acid/bovine calf serum solutions." Biorheology (2009), 46:31-43.

Finelli, I. et al., "A new viscosupplement based on partially hydrophobic hyaluronic acid: a comparative study." Biorheology (2011), 48:263-275.

Garcia-Lopez J.S. et al., "Autologous serum eye drops diluted with sodium hyaluronate: clinical and experimental comparative study," Acta Ophthalmol, vol. 92, pp. e22-e29, 2014.

Gomis, A. et al., "Effects of Different Molecular Weight Elastoviscous Hyaluronan Solutions on Articular Nociceptive Afferents." Arthritis and Rheumatism, (2004), 50 (1):314-326.

Gomis, A. et al., "Hyaluronan Derivatives and Joint Pain." Hyaluronan: Structure, Metabolism, Biological Activities, Therapeutic Applications (1st Ed. 2005) vol. II (Eds. Balazs, EA, and Hascall, V. C.), Published by Matrix Biology Institute, Edgewater, NJ 07020 (USA), 503-507.

Gomis, A. et al., "Intra-articular injections of hyaluronan solutions of different elastoviscosity reduce nociceptive nerve activity in a model of osteoarthritic knee joint of the guinea pig." Osteoarthritis and Cartilage (2009) 17:798-804.

(56) References Cited

OTHER PUBLICATIONS

Gomis, A. et al., "Nociceptive nerve activity in an experimental model of knee joint osteoarthritis of the guinea pig: Effect of intra-articular hyaluronan application." Pain (2007), 130:126-136.
Gotoh, S. et al., "Effects of the molecular weight of hyaluronic acid and its action mechanisms on experimental joint pain in rats." Annals of the Rheumatic Diseases (1993), 52:817-822.
Gotoh, S. et al., "Experimental knee pain model in rats and analgesic effect of sodium hyaluronate (SPH)." 1988, Folia Pharmacol. Japan, 92:17-27.
Graue E. L. et al., "The Protective Effect of Na-Hyaluronate to Corneal Endothelium," Exp. Eye. Res., vol. 31, pp. 119-127, 1980.
Guillaumie F. et al., "Comparative studies of various hyaluronic acids produced by microbial fermentation for potenital topical ophthalmic applications," Journal of Biomedical Materials Research Part A, pp. 1421-1430, 2009.
Hamano T. et al., "Evaluation of the Effect of the Sodium Hyaluronate Ophthalmic Solution on Tear Film Stability-Non-contact Specular Microsopic Evaluation-," Department of Ophthalmology, Osaka Seamen's Insurance Hospital, pp. 928-932, 1993.
Hoare, T. et al., "Rheological blends for drug delivery. II. Prolongation of nerve blockade, biocompatibility and in vitro-in vivo correlations." J. Biomed. Mater. Res. (2010), 92A: 586-589.
Horkay, F. et al., "Ions in hyaluronic acid solutions." The Journal of Chemical Physics, (2009), 131 (18): 184902-1 to 184902-8.
Iannitti, T et al., "A new highly viscoelastic hyaluronic acid gel: rheological properties, biocompatiblity and clinical investigation in esthetic and restorative surgery." International Journal of Pharmaceutics, (2013), 546: 583-592.
Iannitti, T. et al., "Preliminary histopathological study of intra-articular injection of a novel highly cross-linked hyaluronic acid in a rabbit model of knee osteoarthritis." J. Mol. Histol., (2013), 44(2): 191-201. XP002730225.
Ibrahim et al., "The impact of hyaluronic acid oligomer content on physical, mechanical, and biological properties of divinyl sulfone-crosslinked hyaluronic acid hydrogels." J. Biomed. Mater. Res. (2010), 94A :355-70.
Iester M. et al., "Improvement of the ocular surface using hypotonic 0.4% hyaluronic acid drops in keratoconjuntivitis sicca," Eye, vol. 14, pp. 892-898, 2000.
International Search Report by the International Searching Authority and Written Opinion on PCT/US2016/052743 dated Feb. 27, 2017.
International Search Report by the International Searching Authority on PCT/US2014/045973 dated Oct. 13, 2014.
Johnson M. E. et al., "Effectiveness of sodium hyaluronate eydrops in the treatment of dry eye," Graefe's Arch Clin Exp Ophthalmol, vol. 244, pp. 109-112, 2006.
Kamiya K. et al., "Clinical evaluation of the additive effect of diquafosol tetrasodium on sodium hyaluronate monotherapy in patients with dry eye syndrome a prospective, a randomized, multicenter study," Eye, vol. 26, pp. 1363-1368, 2012.
Kerr et al., "Surface rheological properties of hyaluronic acid solutions." Biorheology (1985), 22:133-144.
Kiss H. J. et al., "Isotonic Glycerol and Sodium Hyaluronate Containing Artificial Tear Decreases Conjunctivochalasis after One and Three Months: A Self-Controlled, Unmasked Study," PLOS One, pp. 1-13, 2015.
Kogan, G. et al., "Hyaluronic acid: a natural biopolymer with a broad range of biomedical and industrial applications", Biotechnol. Lett. (2007), vol. 29, pp. 17-25.
Krause et al., "Rheology of Sodium Hyaluronate under Physiological Conditions." Biomacromolecules (2001), 2:65-69.
Larsen N. E. et al., "Hylashield (2.0 Pa Elastoviscous Hylan Fluid 0.15%) Protective Corneal Shield: Evaluation of Biological and Physical Properties," Ophthalmic Practice, vol. 12, No. 3, pp. 137-140, 1994.
Larsen, N. et al., "Biocompatibility of Hylan Polymers in Various Tissue Compartments." In Polymers in Medicine and Pharmacy, Materials Research Society Spring Meeting, Apr. 17-21, 1995, San Francisco, CA, (Eds Mikos, A. G., Leong, K. W., Radomsky, M.L., Tamada, J. A., and Yaszemski, M. J.), Materials Research Society, Pittsburgh, PA, 149-153.
Lee J. H., et al., "Efficacy of Sodium Hyaluronate and Carboxymethylcellulose in Treating Mild to Moderate Dry Eye Disease," Cornea, vol. 30, No. 2, pp. 175-179, 2011.
Lee J. S. et al., "Comparison of cytotoxicity and wound healing effect of carboxymethylcellulose and hyaluronic acid on human corneal epithelial cells," Int J Ophthalmol, vol. 8, No. 2, pp. 215-221, 2015.
Li Z. et al., "Effects of Eye Drops Containing a Mixture of Omega-3 Essential Fatty Acids and Hyaluronic Acid on the Ocular Surface in Desiccating Stress-induced Murine Dry Eye," Current Eye Research, pp. 1-8, 2014.
Lin H. et al., "Dry eye disease: a review of diagnostic approaches and treatments," Saudi Journal of Ophthalmology, vol. 28, pp. 173-181, 2014.
Lundsgaard, C. et al., "Intra-articular sodium hyaluronate 2 mL versus physiological saline 20 mL versus physiological saline 2 mL for painful knee osteoarthritis: a randomized clinical trial" Scand. J. Rheumatol. (2008) vol. 37, pp. 142-150.
Madrid R. et al., "Contribution of TRPM8 Channels to Cold Transduction in Primary Sensory Neurons and Peripheral Nerve Terminals," The Journal of Neuroscience, vol. 26, No. 48, pp. 12512-12525, 2006.
Matsuo, Toshihiko, "Trehalose Versus Hyaluronan or Cellulose in Eyedrops for the Treatment of Dry Eye," Jpn J Ophthalmol, vol. 48, pp. 321-327, 2004.
Matteini, P. et al., "Structural Behavior of Highly Concentrated Hyaluronan." Biomacromolecules (2009), 10:1516-1522.
Maulvi F. A. et al., "Extended release of hyaluronic acid from hydrogel contact lenses for dry eye syndrome," Journal of Biomaterials Science, Polymer Edition, 27 pages, 2015.
McDonald, CC. et al., "A randomised, crossover, multicentre study to compare the performance of 0.1% (w/v) sodium hyaluronate with 1.4% (w/v) polyvinyl alcohol in the alleviation of symptons associate with dry eye syndrome," Eye, vol. 16, pp. 601-607, 2002.
Morshirfar M. et al., "Artificial tears potpourri: a literature review," Clincal Ophthalmology, vol. 8, pp. 1419-1433, 2014.
Nepp J. et al., "The clinical use of viscoelastic artificial tears and sodium chloride in dry-eye syndrome," Biomaterials, vol. 22, pp. 3305-3310, 2001.
Oka M. et al., "Effects of High Molecular Weight Hyaluronate on the Lubrication Mechanism of the Joint." Journal of Japanese Society for Rheumatism Joint Surgery 1993, vol. XII, No. 3, pp. 259-266.
Papa V. et al., "Comparison of Hypotonic and Isotonic Solutions Containing Sodium Hyaluronate on the Symptomatic Treatment of Dry Eye Patients," Ophthalmologica, vol. 215, pp. 124-127, 2001.
Parra, A. et al., "Ocular surface wetness is regulated by TRPM8-dependent cold thermoreceptros of the cornea," Nature Medicine, vol. 16, No. 12, pp. 1396-1399, 2010.
Pauloin T. et al., "High molecular weight hyaluronan decreases UVB-induced apoptosis and inflammation in human epithelial corneal cells," Molecular Vision, vol. 15, pp. 577-583, 2009.
Pauloin T. et al., "In vitro modulation of preservative toxicity: High molecular weight hyaluronan decreases apoptosis and oxidative stress induced by benzalkonium chloride," European Journal of Pharmaceuticals Sciences, vol. 34, pp. 263-273, 2008.
Pena, E. et al., "Elastoviscous substances with analgesic effects on joint pain reduce stretch activated ion channel ativity in vitro." Pain (2002), 99:501-508.
Polack F. M. et al., "Penetrating Keroplasty Using MK Stored Corneas and Na Hyaluronate (Healon®)," Tr. Am. Ophth. Soc. vol. 80, pp. 248-261, 1982.
Polack F. M. et al., "Sodium Hyaluronate (Healon®) in Keratoplasty and IOL Implantation," Ophthalmology, vol. 88, No. 5, pp. 425-431, 1981.
Polack F. M. et al., "The Treatment of Dry Eyes with Na Hyaluronate (Healon®)," Cornea, vol. 1, No. 2, pp. 133-136, 1982.
Pozo, M. et al., "Reduction of sensory responses to passive movements of inflamed knee joints by hylan, a hyaluronan derivative." Exp. Brain Res., (1997), 116: 3-9.

(56) References Cited

OTHER PUBLICATIONS

Printed brochure and product descriptions for Innovative 3D Matrix Products for Scientific Research, Advanced Biomatrix. Available at https://www.advancedbiomatrix.com/, last accessed Dec. 3, 2015. 24 pages.
Product Description for Acquafiller Dermal Filler Hylauronic Acid Fine Wrinkles 35mg/ml + Lidocaine 2%-2ml, available at http://acquafiller.com/acquafiller-dermal-filler-hyaluronic-acid-fine-wrinkles-35mg-ml-lidocaine-2-2ml.html, last accessed Nov. 24, 2015.
Product Description for Acquafiller Dermal Filler Hylauronic Acid Fine Wrinkles 45mg/ml + Lidocaine 2%-2ml, available at http://acquafiller.com/acquafiller-dermal-filler-hyaluronic-acid-fine-wrinkles-45mg-ml-lidocaine-2-2ml.html, last accessed Dec. 1, 2015.
Product Description for Acquafiller Dermal Filler Hylauronic Acid Plus 45mg/ml + Lidocaine 2%-2ml, available at http://acquafiller.com/acquafiller-dermal-filler-hyaluronic-acid-plus-45mg-ml-lidocaine-2-2ml.html, last accessed Dec. 1, 2015.
Rah M. J. et al., "A review of hyaluronan and its ophthalmic applications," Optometry, vol. 82, pp. 38-43, 2011.
Saeed N. et al., "Effectiveness of sodium hyaluronate eye gel in patients with dry eye disease: A multi-centre, open label, uncontrolled study," Pak J Med Sci, vol. 29, No. 4, pp. 1055-1058, 2013.
Santoro, S. et al., "Rheological properties of cross-linked hyaluronic acid dermal fillers." J. Appl. Biomater. Biomech (2011), 9(2):127-136.
Shimmura S. et al., "Sodium hyaluronate eyedrops in the treatment of dry eyes," British Journal of Ophthamology, vol. 79, pp. 1007-1011, 1995.
Simmons P. A. et al., "Efficacy and safety of two new formulations of artificial tears in subject with dry eye disease: a 3-month, multicenter, active-controlled, randomized trial," Clinical Ophthalmology, vol. 9, pp. 665-675, 2015.
Snibson G. R. et al., "Precorneal Residence Times of Sodium Hyaluronate Solutions Studied by Quantitative Gamma Scintigraphy," Eye, vol. 4, pp. 594-602, 1990.
Stuart J. C. et al., "Dilute Sodium Hyaluronate (Healon) in the Treatment of Ocular Surface Disorders," Annals of Ophthamology, vol. 17, No. 3, 190-192, 1985.
Tanaka M. et al., The Effect of High-molecular-weight Hyaluronic Acid on Osteoarthritis of the Knee, Journal of Japanese Society for Rheumatism Joint Surgery], 2006, vol. XXV, No. 2, pp. 103-111.
Tascioglu, F. et al., "Efficacy of intra-articular sodium hyaluronate in the treatment of knee osteoarthritis," Clin Rheumatol., vol. 22, pp. 112-117, 2003.
Teping C. et al., "Treatment of Sicca Syndrome—Effective and well-tolerated also with contact lenses," Drug Report, Hyaluronic acid, vol. 4, No. 2, pp. 1-15, 2010.
Tong L. et al., "Choice of Artificial Tear Formulation for Patients With Dry Eye: Where Do We Start?," Cornea, vol. 31, No. 10, pp. S32-S36, 2012.
Troiano P. et al., "Effect of Hypotonic 0.4% Hyaluronic Acid Drops in Dry Eye Patients: A Cross-Over Study," Cornea, vol. 27, No. 10, Dec. 2008, pp. 1126-1130.
Vogel R. et al., "Demonstration of Efficacy in the Treatment of Dry Eye Disease with 0.18% Sodium Hyaluronate Ophthalmic Solution (Vismed, Rejena)," American Journal of Ophthalmology, vol. 149, No. 4, pp. 594-601, 2010.
Vsevolodovich V. et al., "Use of preservative-free hyaluronic acid (Hylabak®) for a range of patients with dry eye syndrome: experience in Russia," Clinical Ophthalmology, vol. 8, pp. 1169-1177, 2014.
Weiss, C. et al., "Basic Principles Underlying the Development of Viscosupplementation for the Treatment of Osteoarthritis." J. Clin. Rheumatol. (1999), 5:S2-S11.
White C. J. et al., "Bringing comfort to the masses: A novel evaluation of comfort agent solution properties," Contact Lens & Anterior Eye, vol. 37, pp. 81-91, 2014.
Williams D. L. et al., "A Crosslinked HA-Based Hydrogel Ameliorates Dye Eye Symptoms in Dogs," International Journal of Biomaterials, vol. 2013, pp. 1-8, 2013.
Wysenbeek Y.S. et al., "The Effect of Sodium Hyaluronate on the Corneal Epithelium," Investigative Ophthalmology & Visual Science, vol. 29, No. 2, pp. 194-199, 1988.
Y. Mo .et al., "Effects of sodium chloride, guanidine hydrochloride, and sucrose on the Viscoelastic Properties of Sodium Hyaluronate Solutions" Biopolymers (1999), vol. 50, pp. 23-34.
Ye J. et al., "High molecular weight hyaluronan decreases oxidative DNA damage induced by EDTA in human corneal epithelial cells," Eye, vol. 26, pp. 1012-1020, 2012.
Yokoi N. et al., "Effectiveness of hyaluronan on corneal epithelial barrier function in dry eye," British Journal of Ophthalmology, vol. 81, pp. 533-536, 1997.
Young et al., "Clinical Comparison of two hyaluronic acid-derived fillers in the treatment of nasolabial folds.", International Journal of Dermatology, May 2012, vol. 51, No. 5 pp. 601-608.
Zhao, X., "Synthesis and characterization of a novel hyaluronic acid hydrogel." J. Biomater. Sci. Polymer Edn, (2006), 17(4):419-433.
Zheng X. et al., "Comparison of in Vivo Efficacy of Different Ocular Lubricants in Dry Eye Animal Models," Invest Ophthalmol Vis Sci, vol. 55, No. 6, pp. 3454-3460, 2014.

* cited by examiner

COMPOSITIONS OF HYALURONAN WITH HIGH ELASTICITY AND USES THEREOF

RELATED APPLICATIONS

This application is a continuation of U.S. application Ser. No. 14/327,321, filed on Jul. 9, 2014, which claims priority to U.S. Provisional Application No. 61/844,645, filed on Jul. 10, 2013. The entire contents of each of the foregoing applications are hereby incorporated herein by reference.

BACKGROUND OF THE INVENTION

Hyaluronan (HA) is a high average molecular weight linear polysaccharide which is found primarily in the extracellular matrix and pericellular matrix, but has also been shown to occur intracellularly. The biological functions of HA include maintenance of the elastoviscosity of liquid connective tissues such as joint synovial fluid and eye vitreous, control of tissue hydration and water transport, supramolecular assembly of proteoglycans in the extracellular matrix, and numerous receptor-mediated roles in cell detachment, mitosis, migration and tumor development.

The analgesic effect of HA solutions on joint pain receptors is well documented. It has been previously suggested that HA of high average molecular weight, when injected intra-articularly, may be the most effective at reducing joint pain. There is experimental evidence to suggest that high average molecular weight hyaluronan acts as an elastoviscous filter, buffering the transmission of mechanical forces to ion channels responsible for the detection of injurious stimuli in joint pain nerve endings, thereby decreasing their excitation. However, the type of interaction between HA molecules and ion channels leading to a change in the excitability of pain nerve endings is unknown. Also, the rheological properties of HA solutions that are most appropriate to maximize their analgesic effects on joint pain receptors have not been fully investigated.

Pain associated with joint function, including pain associated with knee joint function and osteoarthritis, can be treated by injection of compositions that include hyaluronan into the painful joint. However, current treatment methods do not result in a complete suppression of the pain or uniform reduction of pain in all patients. Hyaluronan-based compositions with improved properties are, therefore, needed in the art.

SUMMARY OF THE INVENTION

The present inventors have discovered that compositions comprising high concentrations of HA, e.g., compositions having HA concentrations of about 30 mg/mL (about 3% weight/volume), or greater are surprisingly effective at treating joint pain. In fact, such HA compositions are significantly more effective at treating joint pain than Synvisc®, the most successful HA commercial product currently used for viscosupplementation. Without wishing to be bound by a specific theory, it is believed that the effectiveness of the HA compositions of the invention comprising high concentrations of HA at treating joint pain is determined by their high elasticity, as is evidenced by the high value of the elastic modulus G'. It is also believed, without wishing to be bound by a specific theory, that the effectiveness of the HA compositions of the invention is determined by a relatively high probability of interaction of HA molecules with pain transducing channels, such as TRPV1, thereby reducing nociceptor excitability.

Accordingly, the present invention provides compositions comprising hyaluronan, wherein the hyaluronan is present in the composition at a concentration of greater than about 30 mg/mL; the hyaluronan has an average molecular weight of between about 1 and about 2 million; the hyaluronan is not cross-linked and/or is substantially free of chemical modifications; and wherein the composition is substantially free of other pharmaceutically active substances.

In one embodiment, the other pharmaceutically active substance is a protein. In another embodiment, the other pharmaceutically active substance is a glycosaminoglycan that is different from hyaluronan. In yet another embodiment, the other pharmaceutically active substance is hydroxypropyl methyl cellulose. In a further embodiment, the other pharmaceutically active substance is a local anesthetic, e.g., lidocaine or bupivacaine.

In some embodiments, hyaluronan is present in the composition at a concentration of about 40 mg/mL, about 45 mg/mL, about 50 mg/mL, about 55 mg/mL or about 60 mg/mL.

In one embodiment of the invention, the composition has an elasticity of at least about 200 Pascal when measured at a frequency of 0.5 Hz, or an elasticity of at least about 1,000 Pascal when measured at a frequency of 0.5 Hz. In another aspect, the composition has an elasticity of at least about 2,000 Pascal when measured at a frequency of 0.5 Hz, or an elasticity of at least about 4,000 Pascal when measured at a frequency of 0.5 Hz.

In another aspect, the present invention provides a pharmaceutical composition comprising hyaluronan, wherein the hyaluronan is present in the composition at a concentration of about 40 mg/mL; the hyaluronan has an average molecular weight of between about 1 and about 2 million; the hyaluronan is not cross-linked and/or is substantially free of chemical modifications; and wherein the composition is substantially free of other pharmaceutically active substances.

In one embodiment, the other pharmaceutically active substance is a protein. In another embodiment, the other pharmaceutically active substance is a glycosaminoglycan that is different from hyaluronan. In yet another embodiment, the other pharmaceutically active substance is hydroxypropyl methyl cellulose. In a further embodiment, the other pharmaceutically active substance is a local anesthetic, e.g., lidocaine or bupivacaine.

In one embodiment of the invention, the composition has an elasticity of at least about 200 Pascal when measured at a frequency of 0.5 Hz, or an elasticity of at least about 1,000 Pascal when measured at a frequency of 0.5 Hz. In another aspect, the composition has an elasticity of at least about 2,000 Pascal when measured at a frequency of 0.5 Hz, or an elasticity of at least about 4,000 Pascal when measured at a frequency of 0.5 Hz.

In one embodiment, the compositions of the invention are sterile. In another embodiment, the compositions are suitable for injection into a subject's joint, e.g., the knee, elbow, hip or other appendicular or axial joints.

The present invention also provides methods of reducing at least one symptom associated with joint dysfunction. The methods comprise administering to a subject in need thereof a therapeutically effective amount of a composition of the invention, thereby reducing the at least one symptom associated with joint dysfunction.

In some embodiments, the joint dysfunction is joint pain or joint dysfunction associated with osteoarthritis, postarthroscopy, post-orthoplasty, post-injury or prolonged immobilization. In a specific embodiment, the joint dysfunction is joint pain.

In some embodiments, the administering of the composition of the invention causes a reduction, e.g., at least a two-fold, at least a three-fold, at least a four-fold or at least a five-fold reduction, in the number of nerve impulses induced by normal and abnormal movements in an experimental rat model of osteoarthritis.

In some embodiments, the administering of the HA composition of the invention causes a reduction, e.g., at least a two-fold, at least a three-fold, at least a four-fold, at least a five-fold, at least a six-fold, at least a seven-fold or at least an eight-fold reduction, in the number of nerve impulses induced by normal movements in an experimental rat model of osteoarthritis.

In some embodiments, the administering of the HA composition causes a reduction, e.g., at least a two-fold, at least a three-fold or at least a four-fold reduction, in the number of nerve impulses induced by abnormal movements in an experimental rat model of osteoarthritis. In a specific embodiment, the reduction is greater than the reduction caused by administering a comparable amount of Synvisc®.

In some embodiments, the HA composition is administered by intra-articular injection.

In another aspect, the present invention provides a pre-filled syringe, e.g., a sterile syringe, comprising the HA composition of the invention, as well as kits comprising such pre-filled syringes.

The present invention is further illustrated by the following detailed description and drawings.

BRIEF DESCRIPTION OF THE DRAWINGS

FIG. 1, Panel B is a graph showing G' values (in Pascal) as a function of frequency (in Hz) for HA compositions of the invention (Elastovisc™). This Figure demonstrates that the compositions of the invention are characterized by much higher G' values than any of the tested HA commercial products.

FIG. 2, Panel B is a graph showing the mean number of nerve impulses per movement in inflamed joints as a function of molecular weight for 4% HA compositions of the invention.

FIG. 2, Panel C is a graph showing the mean number of nerve impulses per movement in inflamed joints as a function of HA concentration.

FIG. 2, Panel D is a bar graph showing the mean number of nerve impulses per movement in inflamed joints for various tested HA compositions.

FIG. 5, Panel B shows the percent difference in the mean total number of impulses per movement measured after saline or 4% HA injection, at different times following injection.

FIG. 6, Panel B is a bar graph showing the mean values of movement-evoked impulses per movement measured in un-injected intact joints and in intact joints injected with a 4% HA composition of the invention 24 hours earlier.

FIG. 6, Panel C is a graph showing the time course of the decrease in movement-evoked activity in two different joint nociceptor fibers of different rats following intra-articular injection of a 4% HA composition into an intact knee joint.

FIG. 8, Panels B1 and B2 show intracellular calcium rises evoked in DRG adult neurons by heat after perfusion with saline (B1) or 400 μg/mL HA (B2). Panel B3 shows the ratio of average amplitude change between responses evoked by successive heat pulses in control saline solution and during perfusion with 400 μg/mL HA for DRG adult neurons.

FIG. 8, Panels C1 and C2 show intracellular calcium rise in a HEK-TRPV1-EYFP (+) cell in response to 100 nM capsaicin and 10 μM Carbachol in control solution (C1) and under exposure to 400 μg/mL HA (C2). Panel C3 shows the average amplitude of the response to capsaicin (filled bars) and Carbachol (striped bars) in HEK-TRPV1-EYFP (+) cells during perfusion with control saline solution and in the presence of HA.

FIG. 8, Panels D1 and D2 show intracellular calcium responses of DRG adult sensory neurons to 100 nM capsaicin and 30 mM KCl during perfusion with saline (D1) and with 400 μg/mL HA (D2). Panel D3 shows the average amplitude of the intracellular calcium responses to capsaicin (filled bars) or KCl (striped bars) in control saline solution and in the presence of HA.

FIG. 9, Panel B shows the average current measured at +80 mV potential, obtained from I-V curves shown in Panel A.

FIG. 9, Panel C shows values of different parameters measured from the ramps, fitted with a function that combines a linear conductance multiplied by a Boltzmann activation term, $I = g \times (V - E_{rev})/(1 + \exp((V_{1/2} - V)/S))$.

FIG. 9, Panel D shows the whole-cell currents measured at −60 mV potential, in response to 1 μM capsaicin, in control conditions (top trace), and in cells pre-incubated for 30 minutes and continuously perfused with HA (bottom trace).

FIG. 9, Panel E shows average values of peak currents in HEK-293-TRPV1 cells evoked by capsaicin at −60 mV in saline and in the presence of HA.

FIG. 10, Panel B shows a sample recording of single-channel activity from cells incubated in HA and recorded under perfusion with HA solution. The insets represent single channel amplitude probability histograms of each recording.

FIG. 10, Panel C shows I-V curves obtained in control conditions (black squares) and after exposure to HA (gray circles).

FIG. 10, Panel D shows single channel amplitudes obtained from individual patches, represented as squares (control) and circles (HA-treated).

FIG. 10, Panel E shows the probability of the open state for different patches. Larger symbols represent the data from the measurements performed in the traces shown in Panels A and B.

FIG. 11, Panel B shows a sample record of capsaicin stimulation in a DRG neuron treated with HA and recorded in the presence of HA.

FIG. 11, Panel C shows a sample record in a DRG neuron treated with HA, in which the response to capsaicin was abrogated while a normal response to KCl was still evoked.

FIG. 11, Panel D shows the mean firing frequency (left) and individual data (right) of DRG neurons under control conditions and after exposure to HA.

FIG. 13, Panel B is an expanded trace for one of the nerve fibers activated by the joint movement. Panel B shows that this nerve fiber is recruited by a rapid, bolus injection of capsaicin into the joint artery (upper trace). Following an intra-articular injection of HA, the response to capsaicin decreases gradually over time (medium trace, 180 min; lower trace, 240 min).

FIG. 13, Panel C is a graph showing the mean values of the firing response to intra-arterial capsaicin, measured in animals that received an injection of intra-articular saline (filled squares) or HA (open squares).

DETAILED DESCRIPTION OF THE INVENTION

Figure 1:
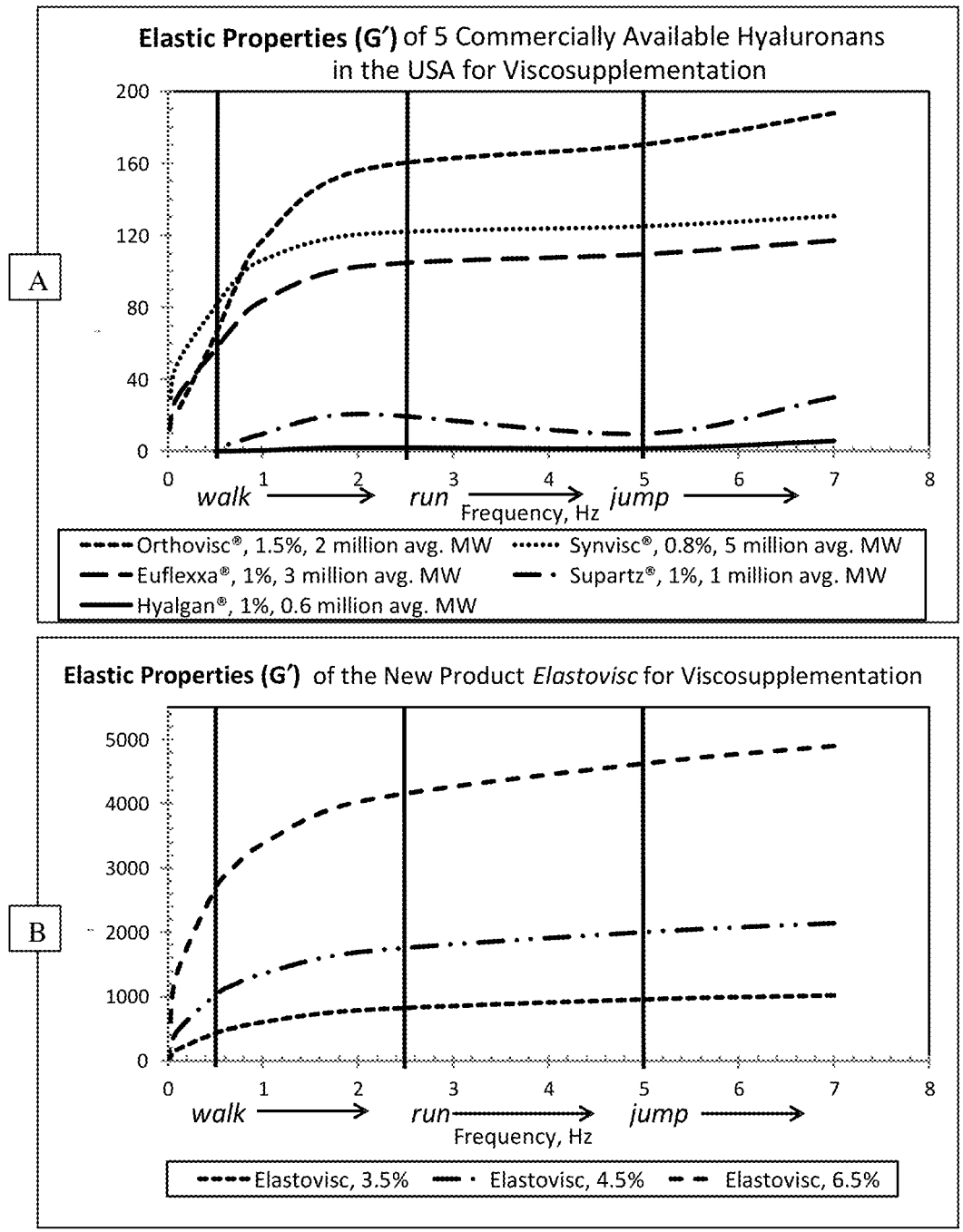
FIG. 1, Panel A is a graph showing G' values (in Pascal) as a function of frequency (in Hz) for commercially available HA compositions used for viscosupplementation.

The present invention provides compositions comprising high concentrations of hyaluronan (HA). Such compositions were determined to have high elasticity, e.g., high elastic modulus G', when measured at frequencies of 0.1-10 Hz. It has been presently discovered that HA compositions characterized by high elasticity, e.g., compositions comprising high concentrations of HA, are surprisingly effective at treating joint pain, such as joint pain caused by osteoarthritis. The average molecular weight of HA comprised in the compositions of the invention may be 2 million or less, e.g., between about 1-2 million.

The above discovery was unexpected because it was previously believed that the effectiveness of HA compositions in treating joint pain was dependent on the average molecular weight of HA, and not on its concentration. In particular, it was believed that high average molecular weight HA compositions, e.g., compositions comprising HA having an average molecular weight of greater than 2 million, were the most effective for treating joint pain.

Hyaluronan (also called hyaluronic acid or hyaluronate or HA) is a glycosaminoglycan present in joint fluid and in the synovial tissue around it. This highly elastoviscous, polydisperse polysaccharide is a major component of the synovial fluid that fills the intercellular space in the synovium, the connective tissue that surrounds the joint space.

The elastoviscous properties of synovial fluid are critical to its physiological functions. Synovial fluid must be capable of viscous flow to participate in the fluid movements that are critical for intra-articular metabolism. However, the same synovial fluid must also behave as a shock absorber, using its elastic properties to store the impact of mechanical stress on the joint in a way that limits the deformation of tissue surfaces, fibrous structures, nerve endings and cells.

The ability of HA contained in the synovial fluid and tissues to modulate the response of a joint to different types of movements is explained by the fact that HA possesses both viscous and elastic properties. During slow movement, the synovial fluid that fills the tissue is exposed to low deformation frequencies and the rate at which energy is transmitted to the hyaluronan network is low enough to allow time for the hyaluronan molecules to adjust their configuration and line up in the direction of flow. Thus, during slow movement, the energy applied to the synovial fluid is predominantly dissipated as viscous flow and heat. This alignment of hyaluronan molecules is also responsible for the pseudoplasticity of synovial fluid (shear thinning, or the decrease in viscosity with increasing flow rate). However, when the hyaluronan network in synovial fluid is subjected to a high rate of deformation, such as during running or jumping, the stress is transferred rapidly and so the hyaluronan molecules have insufficient time to adjust their configuration. Instead, HA acts as coiled molecular shock absorber, storing the energy transmitted as elastic deformation, and behaving like an elastic solid.

The strain frequency of the applied mechanical stress determines whether the hyaluronan acts predominantly as a viscous fluid or an elastic shock absorber. Two values are used to describe the rheological profile of an elastoviscous fluid: the elasticity modulus, G', is a measure of elasticity, while the viscosity modulus, G", is a measure of viscosity. When HA is subjected to a high rate of deformation (e.g., during running or jumping), the HA molecules act as a coiled molecular shock absorber and behave like an elastic solid. When HA is subjected to a low rate of deformation (e.g., during slow movement), the energy applied to the synovial fluid is dissipated as viscous flow and heat.

In the 1960s, it was discovered that hyaluronan, when injected into inflamed knee joints, reduces pain. As a result of this discovery, highly purified HA solutions were developed for the treatment of arthritic pain in humans and animals. This new therapeutic use was called viscosupplementation. HA can act as an elastoviscous cover, reducing the mechanical force reaching the ion channels responsible for the activation of the pain nerve fibers by noxious stimuli, thereby reducing the opening probability of certain channels, decreasing the number of nerve impulses in pain terminals and, thus, reducing pain sensations. It was also shown that an increase of protection for the pain receptors improves the healing processes in the joint.

The average molecular weight of hyaluronan in human synovial fluid of a healthy individual is between 3-4 million, while the average molecular weight of hyaluronan in the pathological joint is between 0.5 to 2 million. It was thought that hyaluronan used in the treatment of joint pain, e.g., joint pain associated with osteoarthritis, had to have a similar or even higher average molecular weight than the hyaluronan present in the healthy joint. In order to reduce pain and inflammation a hyaluronan of high average molecular weight was used that was the same size or larger as present in the joint prior to the joint becoming pathological (painful).

In the synovial fluid of healthy human knee joints, hyaluronan is found at an average concentration of around 321 mg/100 mL (range of 250-368/mg/100 mL). In pathological joints, the synovial fluid has been found to have a lower concentration, mostly between 40-188 mg per 100 mL. It was also thought that hyaluronan used in the treatment of joint pain, e.g., in joint pain associated with osteoarthritis, had to be administered at the same or even a higher concentration as the hyaluronan present in the healthy joint. Commercially available hyaluronan compositions for injection into a painful or otherwise pathological joint have a concentration of up to 2.2% (22 mg/mL). Thus, the concentration of hyaluronan in compositions available for injection into the joint is much greater than the concentration of hyaluronan in healthy joints.

There are several hyaluronan products on the market worldwide for the improvement of joint function and the treatment of pain associated with joint function (see e.g., Table 1 in Example 1). These products generally have a high average molecular weight of hyaluronan and a relatively low concentration (1-2.2%). As noted above, hyaluronan in human synovial fluid of a healthy individual is between 3-4 million average molecular weight. It was thought that hyaluronan with a high average molecular weight would be the most effective in the treatment of joint pain.

The ultrapure hyaluronan product Synvisc® (described, for instance, by Endre A. Balazs in U.S. Pat. No. 4,141,973), is the hyaluronan product with the highest average molecular weight available for viscosupplementation (5 million), was found to be the most active "pain killer" in pathological animal and human joints. Synvisc® also contains 20% of a cross-linked, highly hydrated hyaluronan gel. Synvisc® reduces the impulse activity in sensory fibers evoked by movements in normal and inflamed joints, thereby reducing the pain associated with joint function. Synvisc® is thought to be the most effective of the currently available commercial HA products in the treatment of pain. However, the production of sterile hyaluronan with high average molecular weight is challenging, and this is believed to be a reason that all commercially available hyaluronan products except Synvisc® have a significantly lower average molecular weight.

Many hyaluronan products currently on the market have a concentration of hyaluronan of about 0.8% (Synvisc®), 1.0% (Euflexxa®, Supartz®, Hyalgan®, Gel-One®, Synocrom®, Synocrom® Mini), 1.5% (Orthovisc®), 2% (Synocrom® Forte, Synocrom® Forte One, Synolis V-A) or 2.2% (Monovisc®). These hyaluronan products have a percentage of hyaluronan not higher than 0.8-2.2%, because such a concentration is already much higher than the concentration in healthy tissue. It was assumed in the art that concentrations even higher than 0.8-2.2% would be too high compared to the hyaluronan concentration in the healthy human joint.

It has now been recognized for the first time that inflamed and painful joints are more responsive to HA compositions of high elasticity than to HA compositions with low elasticity. Accordingly, the present invention provides compositions of hyaluronan with high elastic properties and shows the superior properties in the treatment of joint pain of compositions of hyaluronan with high elastic properties (e.g., Elastovisc™) as compared to currently available compositions of hyaluronan with low elasticity. The compositions of hyaluronan with high elastic properties disclosed herein (e.g., Elastovisc™) are based on the discovery that the anti-pain effect of hyaluronan in the joint does not depend on the viscosity of the product, but on its elasticity. Consequently, the therapeutic success of the compositions of hyaluronan disclosed herein depends on the elasticity of the hyaluronan compositions used. While not being limited to a particular mechanism, it is thought that the high elasticity hyaluronan concentrations provided herein, persist in the joint for a long time (e.g., weeks or longer), and influence not only the pain receptors, but interact with and/or remove pain-causing chemical agents.

As disclosed herein, in one embodiment, compositions of hyaluronan with high elasticity can be generated by increasing the concentration of the hyaluronan in the compositions. It is unexpectedly shown herein that compositions of hyaluronan with a high concentration of hyaluronan, even with an average molecular weight of 1-2 million, can be used in the treatment of joint pain. This result is unexpected because prior to the instant invention it was thought that only high average molecular weight compositions of hyaluronan (e.g., Synvisc®) could have a strong pain reducing effect. The result is further unexpected because prior to the instant invention it was thought that concentrations greater than 0.8-2.2% (which are already much higher than the concentrations found in the healthy joint), would have no additional beneficial effects or could even be too high in comparison with the concentration in the healthy joint. Additionally, the present inventors have discovered that the high concentration of HA molecules facilitates their interaction with TRPV1 channels of nociceptors, thereby reducing the responsiveness of the nociceptors to noxious stimuli.

I. Hyaluronan Compositions of the Invention

The present invention provides pharmaceutical compositions comprising hyaluronan (HA). In some embodiments, a composition of the invention comprises hyaluronan, wherein the hyaluronan is present in the composition at a concentration of greater than about 30 mg/mL (or greater than about 3% weight/volume); the hyaluronan has an average molecular weight of between about 1 and about 2 million; the hyaluronan is not cross-linked and/or is substantially free of chemical modifications; and wherein the composition is substantially free of other pharmaceutically active substances.

For example, the HA concentration in the compositions of the invention may be about 30 mg/mL (or about 3% w/v), about 35 mg/mL (or about 3.5% w/v), about 40 mg/mL (or about 4% w/v), about 45 mg/mL (or about 4.5% w/v), about 50 mg/mL (or about 5% w/v), about 55 mg/mL (or about 5.5% w/v), about 60 mg/mL (or about 6% w/v), about 65 mg/mL (or about 6.5% w/v), about 70 mg/mL (or about 7% w/v), about 75 mg/mL (or about 7.5% w/v), about 80 mg/mL (or about 8% w/v), about 85 mg/mL (or about 8.5% w/v), about 90 mg/mL (or about 9% w/v), about 95 mg/mL (or about 9.5% w/v), about 100 mg/mL (or about 10% w/v), about 105 mg/mL (or about 10.5% w/v), about 110 mg/mL (or about 11% w/v) about 115 mg/mL (or about 11.5% w/v), about 120 mg/mL (or about 12% w/v), about 125 mg/mL (or about 12.5% w/v), about 130 mg/mL (or about 13% w/v), about 135 mg/mL (or about 13.5% w/v), about 140 mg/mL (or about 14% w/v), about 145 mg/mL (or about 14.5% w/v), or about 150 mg/mL (or about 15% w/v). In a specific embodiment, the HA is present in the composition at a concentration of about 40 mg/mL (or about 4% w/v). In another specific embodiment, the HA is present in the composition of the invention at the concentration of about 60 mg/mL (or about 6% w/v).

In certain embodiments, the hyaluronan used in the compositions of the invention is not cross-linked and/or is free of chemical modifications. For example, the hyaluronan used in the compositions of the invention is free from amidation that may be formed by a reaction between the carboxyl group of HA and the amine group of a derivatizing agent as described, e.g., in EP Patent No. 1095064 B1. The hyaluronan used in the compositions of the invention may also be free from chemical modifications and/or cross-links that may result from the reaction of hyaluronan with a carbodiimide, such as a monocarbodiimide or a biscarbodiimide, as described, for example, in U.S. Pat. No. 8,323,617.

In some embodiments, the HA compositions of the invention are free from other pharmaceutically active substances. As used herein, a "pharmaceutically active substance" is a substance that is capable of exerting a biological effect on a subject, e.g., a human or an animal subject. This term "pharmaceutically active substance" also comprises substances that can modulate the biological effect of an HA composition when the composition is administered to a subject, e.g., modulate the ability of the HA composition to reduce pain in an inflamed joint. In certain embodiments, the pharmaceutically active substance is a protein, e.g., a bone morphogenic protein (BMP), such as rhGDF-5. In certain embodiments, the pharmaceutically active substance is a glycosaminoglycan (GAG) that is different from HA, e.g., chondroitin. In some embodiments, the pharmaceutically active substance is hydroxypropyl methyl cellulose. In other embodiments, the pharmaceutically active substance is a topical anesthetic, such as a lidocaine or a bupivacaine.

In certain embodiments, the HA compositions of the invention are free from molecules capable of scavenging free radicals, such as sorbitol. In other embodiments, the HA compositions of the invention are free from molecules that diminish the elasticity of HA, for example, dextran or sucrose.

In some embodiments, an HA composition of the invention consists essentially of HA present at a concentration of greater than about 30 mg/mL (about 3% w/v), or about 40 mg/mL (about 4% w/v) in a physiological buffer, e.g., a phosphate buffer or a bicarbonate buffer, and having the average molecular weight of between about 1 million and about 2 million. In a specific embodiment, an HA composition of the invention consists essentially of HA present at a concentration of about 40 mg/mL (or about 4% w/v), and having the average molecular weight of between about 1 million and about 2 million.

In another embodiment, the HA compositions of the invention may be administered to a subject in need thereof via an injection using an injection device, such as a needle, a trocar, a cannula or a perfusion device. The injection device suitable for injecting the HA compositions of the invention may have a nominal diameter of 2.11 mm or greater (corresponding to 14G needle, or a needle gauge of 14 of greater). In some embodiments, the HA compositions of the invention may be too viscous for administration using smaller needles, e.g., needles having a nominal diameter of less than 2.11 mm. In other embodiments, the HA compositions of the invention may allow administration using smaller injection devices having a nominal diameter of less than 2.11 mm.

For example, a device suitable for injecting the HA compositions of the invention, such as a syringe, may have a nominal diameter of about 0.31 mm, 0.34 mm, 0.36 mm, 0.41 mm, 0.474 mm, 0.46 mm, 0.49 mm, 0.515 mm, 0.51 mm, 0.54 mm, 0.57 mm, 0.59 mm, 0.642 mm, 0.64 mm, 0.67 mm, 0.718 mm, 0.72 mm, 0.77 mm, 0.82 mm, 0.87 mm, 0.91 mm, about 0.99 mm, about 1.07 mm, about 1.17 mm, about 1.27 mm, about 1.42 mm, about 1.47 mm, about 1.57 mm, about 1.65 mm, about 1.73 mm, about 1.83 mm, about 1.98 mm, about 2.11 mm, about 2.26 mm, about 2.41 mm, about 2.54 mm or about 2.77 mm, corresponding, respectively, to gauge of 30, 29, 28, 27, 26s, 26, 25.5, 25s, 25, 24.5, 24, 23.5, 23s, 23, 22.5, 22s, 22, 21.5, 21, 20.5, 20, 19.5, 19, 18.5, 18, 17.5, 17, 16.5, 16, 15.5, 15, 14.5, 14, 13.5, 13, 12.5 or 12 (or 30G, 29G, 28G, 27G, 26sG, 26G, 25.5G, 25sG, 25G, 24.5G, 24G, 23.5G, 23sG, 23G, 22.5G, 22sG, 22G, 21.5G, 21G, 20.5G, 20G, 19.5G, 19G, 18.5G, 18G, 17.5G, 17G, 16.5G, 16G, 15.5G, 15G, 14.5G, 14G, 13.5G, 13G, 12.5G or 12G needles). In one embodiment, the HA compositions of the invention may be administered using an 18G syringe needle having a nominal diameter of about 1.27 mm. In some embodiments, the HA compositions of the invention may be too viscous for administration using smaller needles, e.g., needles having a nominal diameter of.

The hyaluronan in the compositions of the invention may have an elasticity of at least 100 Pascal when measured at a frequency of 0.5 Hz, or an elasticity of at least 400 Pascal when measured at a frequency of 0.5 Hz, or an elasticity of at least 1,000 Pascal when measured at a frequency of 0.5 Hz, or an elasticity of at least 2,000 Pascal when measured at a frequency of 0.5 Hz, or an elasticity of at least 4,000 Pascal when measured at a frequency of 0.5 Hz, or an elasticity of between 400 and 5,000 Pascal when measured at a frequency of 0.5 Hz.

It should be appreciated that a variety of methods are available for measuring the elasticity of a biopolymer such as hyaluronan. In one embodiment, the present invention provides compositions comprising hyaluronan with high elasticity, wherein the elasticity is measured as pressure (expressed in Pascal) at a specific frequency (expressed in Hertz). In some embodiments, the frequencies used herein correspond to a particular joint movement. For instance, the frequencies that may be used to evaluate the elasticity of the hyaluronan compositions provided herein, may be measured at 0.5 Hz (corresponding to walking), 2.5 Hz, (corresponding to running), or 5.0 Hz (corresponding to jumping). These frequencies are applicable to the knee joint, but other joints that have a similar exposure (e.g., hip, ankles) may experience the same stress frequency. Furthermore, while the elasticity may be expressed as a pressure at a specific function associated with knee function (e.g., walking, running), elasticity may also be expressed as pressure exerted by a non-walking movement (e.g., rotation of an elbow or shoulder or a wrist movement).

It should further be appreciated that the elasticity may be expressed in any relevant frequency. Thus, for instance, in one embodiment, the elasticity is expressed based on a "running" frequency of 2.5 Hz and a composition comprising hyaluronan with high elasticity is a composition with an elasticity of at least 200 Pa at a frequency of 2.5 Hz. Similarly, in one embodiment, the elasticity is expressed based on a "jumping" frequency of 5.0 Hz and a composition comprising hyaluronan with high elasticity is a composition having an elasticity of at least 400 Pa at a frequency of 5.0 Hz.

In one aspect, the present invention provides a composition comprising hyaluronan, wherein the composition has an elasticity of at least 100 Pascal when measured at a frequency of 0.5 Hz. In some embodiments, the composition has an elasticity of at least 300 Pascal when measured at a frequency of 2.5 Hz. In some embodiments, the composition has an elasticity of at least 350 Pascal when measured at a frequency of 5.0 Hz.

In one aspect, the present invention provides a composition comprising hyaluronan, wherein the composition has an elasticity of at least 400 Pascal when measured at a frequency of 0.5 Hz. In some embodiments, the composition has an elasticity of at least 750 Pascal when measured at a frequency of 2.5 Hz. In some embodiments, the composition has an elasticity of at least 900 Pascal when measured at a frequency of 5.0 Hz.

In one aspect, the present invention provides a composition comprising hyaluronan, wherein the composition has an elasticity of at least 1000 Pascal when measured at a frequency of 0.5 Hz. In some embodiments, the composition has an elasticity of at least 1600 Pascal when measured at a frequency of 2.5 Hz. In some embodiments, the composition has an elasticity of at least 2000 Pascal when measured at a frequency of 5.0 Hz.

In one aspect, the present invention provides a composition comprising hyaluronan, wherein the composition has an elasticity of at least 2600 Pascal when measured at a frequency of 0.5 Hz. In some embodiments, the composition has an elasticity of at least 4000 Pascal when measured at a frequency of 2.5 Hz. In some embodiments, the composition has an elasticity of at least 4500 Pascal when measured at a frequency of 5.0 Hz.

In one aspect, the present invention provides a composition comprising hyaluronan, wherein the composition has an elasticity of at least 4000 Pascal when measured at a frequency of 0.5 Hz. In some embodiments, the composition has an elasticity of at least 5000 Pascal when measured at a frequency of 2.5 Hz. In some embodiments, the composition has an elasticity of at least 6000 Pascal when measured at a frequency of 5.0 Hz.

In some embodiments, the composition has an elasticity of between 100 and 10,000 Pascal when measured at a frequency of 0.5 Hz. In some embodiments, the composition has an elasticity of between 400 and 5,000 Pascal when measured at a frequency of 0.5 Hz. In some embodiments, the composition has an elasticity of between 1,000 and 2,000 Pascal when measured at a frequency of 0.5 Hz.

In some embodiments, the composition has an elasticity of between 300 and 10,000 Pascal when measured at a frequency of 2.5 Hz. In some embodiments, the composition has an elasticity of between 750 and 6,000 Pascal when measured at a frequency of 2.5 Hz. In some embodiments, the composition has an elasticity of between 1,500 and 4,000 Pascal when measured at a frequency of 2.5 Hz.

In some embodiments, the composition has an elasticity of between 300 and 10,000 Pascal when measured at a frequency of 5.0 Hz. In some embodiments, the composition has an elasticity of between 900 and 7,000 Pascal when measured at a frequency of 5.0 Hz. In some embodiments, the composition has an elasticity of between 2,000 and 5,000 Pascal when measured at a frequency of 5.0 Hz.

In some embodiments, the elasticity is measured by using a suitable device (e.g., a rheometer). In some embodiments, the elasticity is measured by using a Stresstech High Resolution Research Rheometer (Reologica Instruments AB). In some embodiments, the elasticity is determined at ambient temperature and pressure. However, it should be appreciated that elasticity may also be measured at non-ambient temperature and/or pressure. It should further be appreciated that a person of ordinary skill in the art knows how to convert a magnitude of elasticity determined at various temperatures and pressures into a magnitude of elasticity at ambient temperature and pressure.

As disclosed herein, high elasticity compositions of hyaluronan can be prepared by increasing the concentration of hyaluronan in the composition. Thus, in one aspect, the present invention provides compositions having high elasticity that comprise a high percentage of hyaluronan. For example, the compositions of the invention comprise at least 3.0% of hyaluronan (weight by volume), at least 3.5% of hyaluronan (weight by volume), at least 4.0% of hyaluronan (weight by volume), at least 4.5% of hyaluronan (weight by volume), at least 5.0% of hyaluronan (weight by volume), at least 5.5% of hyaluronan (weight by volume), at least 6.0% of hyaluronan (weight by volume), at least 6.5% of hyaluronan (weight by volume), at least 7.0% of hyaluronan (weight by volume), at least 7.5% of hyaluronan (weight by volume), at least 8.0% of hyaluronan (weight by volume), at least 8.5% of hyaluronan (weight by volume), at least 8.9% of hyaluronan (weight by volume), at least 9.0% of hyaluronan (weight by volume), at least 10.0% of hyaluronan (weight by volume), at least 11.0% of hyaluronan (weight by volume), at least 12.0% of hyaluronan (weight by volume), at least 13.0% of hyaluronan (weight by volume), at least 14.0% of hyaluronan (weight by volume), or at least 15.0%, or more, of hyaluronan (weight by volume).

Ranges intermediate to the recited values are also intended to be part of this invention. For example, hyaluronan content in the compositions of the invention may be between about 3% and about 15% (weight/volume), between about 3% and about 10% (weight/volume), about 3.5% and about 9% (weight/volume), about 4% and about 8% (weight/volume), or about 5% and about 7% (weight/volume).

It should further be appreciated that the amount of hyaluronan in a particular volume may also be expressed by alternative means (e.g., gram/liter or mol/liter). A person of ordinary skill in the art would know how to convert the various means of expressing the amount of hyaluronan in a particular volume.

As indicated above, it is unexpectedly shown herein that compositions of hyaluronan with a high concentration of hyaluronan, even with an average molecular weight of about 1-2 million, are particularly effective in the treatment of joint pain. Thus, in some embodiments of the compositions of hyaluronan provided herein, the average molecular weight of hyaluronan is less than 2 million, less than 1.9 million, less than 1.8 million, less than 1.7 million, less than 1.6 million, less than 1.5 million, less than 1.4 million, less than 1.3 million, less than 1.2 million, less than 1.1 million, less than 1 million, less than 0.9 million, less than 0.8 million, less than 0.7 million, less than 0.6 million, or less than 0.5 million.

Ranges intermediate to the recited values are also intended to be part of this invention. For example, in the compositions of hyaluronan provided herein, the average molecular weight of hyaluronan is between 1 and 2 million, between 1 and 1.5 million, between 0.5 and 1 million, between 0.5 and 2 million, or between 0.9 and 1.4 million.

In some embodiments of the compositions of hyaluronan provided herein, the majority of the hyaluronan present in the composition falls within the average molecular weight range provided herein. Thus, for instance, in compositions with an average molecular weight of hyaluronan of between 0.2 and 2 million, at least 95% of the hyaluronan present in the composition falls within the range of between 0.2 and 2 million. In some embodiments, at least 50% of the hyaluronan present in the compositions provided herein falls within the recited range of average molecular weight. In some embodiments, at least 60% of the hyaluronan present in the compositions provided herein falls within the recited range of average molecular weight. In some embodiments, at least 70% of the hyaluronan present in the compositions provided herein falls within the recited range of average molecular weight. In some embodiments, at least 80% of the hyaluronan present in the compositions provided herein falls within the recited range of average molecular weight. In some embodiments, at least 90% of the hyaluronan present in the compositions provided herein falls within the recited range of average molecular weight. In some embodiments, at least 95% of the hyaluronan present in the compositions provided herein falls within the recited range of average molecular weight. In some embodiments, at least 98% of the hyaluronan present in the compositions provided herein falls within the recited range of average molecular weight. In some embodiments, at least 99% of the hyaluronan present in the compositions provided herein falls within the recited range of average molecular weight. In some embodiments, at least 99.9% of the hyaluronan present in the compositions provided herein falls within the recited range of average molecular weight.

II. Sources of Hyaluronan

The hyaluronan used in the compositions and methods provided herein may be obtained from any source. In general, hyaluronan has the same chemical structure, regardless of its origin (e.g., chicken or rooster comb, human or bacterial cell wall). Hyaluronan can be obtained, for instance, from chicken or rooster comb, from bacterial cell walls and from human tissue (vitreous of the eye, synovial fluid from the joints, etc.). In some embodiments, the hyaluronan is isolated from chicken combs. In some embodiments, the hyaluronan is isolated from human tissue e.g., umbilical cord, vitreous of the eye, synovial fluid from the joints. In some embodiments, the hyaluronan is isolated from cell culture. In some embodiments, the hyaluronan is isolated from bacterial cell walls. The isolation of hyaluronan from various sources is known to a person of ordinary skill in the art. For instance, the harvest and purification of hyaluronan from rooster combs is described in U.S. Pat. No. 4,141,973, while the harvest and purification of hyaluronan from bacterial sources is described in U.S. Pat. No. 4,517,295. In some embodiments, the hyaluronan is purified and harvested to a solution with 0.15 M NaCl at a pH of 6-8. Generally, the hyaluronan obtained from the various sources will be free of proteins or glycosaminoglycans other than hyaluronan.

In some embodiments, the isolated hyaluronan is further purified to obtain hyaluronan with a desired average molecular weight range (e.g., through column chromatography). Methods for purifying hyaluronan with a desired average molecular weight range are known to a person of ordinary skill in the art.

In one aspect, the hyaluronan with high elasticity disclosed herein is unmodified hyaluronan. However, it should be appreciated that in some embodiments, the hyaluronan may be chemically modified. For instance, the hyaluronan may be chemically modified to increase the elasticity of the hyaluronan.

III. Sterilization of the Hyaluronan Compositions of the Invention

In some embodiments, the compositions of the invention are sterile. A "sterile composition", as used herein, refers to a composition that is safe to be administered to a subject, e.g., a human subject. Thus, a sterile composition will only have a minimal number of agents that can cause unwanted side effects such as an unwanted immune response, e.g., inflammation or infection.

Methods for sterilizing compositions of hyaluronan are known in the art and include, for example, heat or steam sterilization, e.g., by autoclaving. In some embodiments, the HA compositions of the invention are sterilized by heating the compositions. In some embodiments, the HA compositions of the invention are sterilized by including the HA composition in a syringe and autoclaving the HA containing syringe at 131° C. for 2 minutes or 121° C. for 15 minutes followed by immediate cooling.

IV. Additional Components for the Hyaluronan Compositions of the Invention

The HA compositions of the invention may include additional components that may stabilize the hyaluronan and/or make the composition more suitable for administration to a subject. In some embodiments, the HA compositions of the invention may include a buffer. Buffers are added in order to allow for a stable pH. Suitable buffers for use in the present invention include phosphate buffers and bicarbonate buffers. In some embodiments, the buffer is a tris-phosphate buffer. In some embodiments, the buffer is present in a concentration of between 1 mM and 100 mM, between 2 mM and 50 mM, or between 5 mM and 20 mM. In some embodiments, the buffer concentration is less than 1 mM. In some embodiments, the buffer concentration is more than 100 mM. In some embodiments, the buffer concentration is 10 mM. It should be appreciated that the buffer concentration is dependent on the nature of the buffer that is being used. In some embodiments, the pH of the composition is between pH 7 and pH 9 or between pH 7.5 and pH 8.5. In some embodiments, the pH of the composition is 8.0. In some embodiments, the pH of the composition is 7.5. In some embodiments, the pH of the composition is 8.5. If needed, acid (such as HCL) or base (such as NaOH) can be added to the composition to attain the desired pH.

In some embodiments, the hyaluronan compositions include a buffer, e.g., a physiologically compatible buffer, but do not include any additional components.

In some embodiments, the composition includes a stabilizing excipient, such as carboxylic acid or a salt thereof. In some embodiments, the composition includes a monocarboxylic acid and/or salt thereof. In some embodiments, the composition includes a gluconic acid and/or sodium gluconate. In some embodiments, the composition includes a dicarboxylic acid and/or a salt thereof. In some embodiments, the composition includes a citric acid, succinic acid, malonic acid, maleic acid, tartaric acid and or a salt thereof. In some embodiments, the carboxylic acid is sodium citrate. In some embodiments, the composition includes a tricarboxylic aid and/or a salt thereof. In some embodiments, the composition includes a nitrilotriacetic acid and/or sodium nitrilotriacetic acid. In some embodiments, the composition includes a tetracarboxylic acid and/or salt thereof. In some embodiments, the composition includes a ethylenediaminetetracetic acid (EDTA) and/or sodium EDTA. In some embodiments, the composition includes a pentacarboxylic acid and/or a salt thereof. In some embodiments, the composition includes a diethylenetriaminepentaacetic (DTPA) acid and/or sodium DTPA. Suitable carboxylic acids include, but are not limited to, citrate compounds, such as sodium citrate; tartrate compounds, succinate compounds, and EDTA. Kaushil et al. in Protein Science 1999 8: 222-233, and Busby et al. in the Journal of Biological Chemistry Volume 256, Number 23 pp 12140-1210-12147 describe carboxylic acids and their uses. In some embodiments, the stabilizing excipient has a concentration of between 50 to 600 mM, between 250 to 500 mM, or between 250 to 350 mM. In some embodiments, the concentration of the stabilizing excipient is 300 mM. In some embodiments, the concentration of the stabilizing excipient is less than 100 mM. In some embodiments, the concentration of the stabilizing excipient is more than 600 mM.

In some embodiments, the HA compositions of the invention include a sugar (e.g., a disaccharide sugar). Disaccharide sugars that can be added to the composition include, but are not limited to, sucrose, lactulose, lactose, maltose, trehalose, cellobiose, dextrose and dextran. In some embodiments, the sugar is present at between 0.5 to 5% (wt/volume). In some embodiments, the sugar is present at between 1 to 2% (wt/volume). In one embodiment, the sugar is present at 1%. In some embodiments, the sugar is present at less than 1% (wt/volume). In some embodiments, the sugar is present at more than 5% (wt/volume). In one embodiment, the sugar is sucrose or trehalose and is present at 1% (wt/volume).

In some embodiments, the HA compositions of the invention include salts. Salts that can be used in the compositions include sodium chloride and other physiological compatible salts. In some embodiments, the salt concentration is between 10 mM and 250 mM, between 25 mM and 100 mM. In some embodiments, the salt concentration is 50 mM. In some embodiments, the salt concentration is less than 10 mM. In some embodiments, the salt concentration is more than 250 mM.

In some embodiments, the HA compositions of the invention include one or more antioxidants. Antioxidants are substances capable of inhibiting oxidation by removing free radicals from solution. Antioxidants are well known to those of ordinary skill in the art and include materials such as ascorbic acid, ascorbic acid derivatives (e.g., ascorbylpalmitate, ascorbylstearate, sodium ascorbate, or calcium ascorbate), butylated hydroxy anisole, buylated hydroxy toluene, alkylgallate, sodium meta-bisulfite, sodium bisulfite, sodium dithionite, sodium thioglycollic acid, sodium formaldehyde sulfoxylate, tocopherol and derivatives thereof, (d-alpha tocopherol, d-alpha tocopherol acetate, d-alpha tocopherol succinate, beta tocopherol, delta tocopherol, gamma tocopherol, and d-alpha tocopherol polyoxyethylene glycol 1000 succinate) monothioglycerol and sodium sulfite. Such materials are typically added in ranges from 0.01 to 2.0%.

In some embodiments, the HA compositions of the invention include one or more isotonicity agents. This term is used in the art interchangeably with iso-osmotic agent, and is known as a compound which can be added to a pharmaceutical preparation to increase the osmotic pressure, such as an osmotic pressure of 0.9% sodium chloride solution, which is iso-osmotic with human extracellular fluids, such as plasma. Preferred isotonicity agents to be used in the compositions of the invention include are sodium chloride, mannitol, sorbitol, lactose, dextrose and glycerol.

In some embodiments, the HA compositions of the invention include one or more preservatives. Suitable preservatives include but are not limited to: chlorobutanol (0.3-0.9% w/v), parabens (0.01-5.0%), thimerosal (0.004-0.2%), benzyl alcohol (0.5-5%), phenol (0.1-1.0%), and the like.

In some embodiments, the composition includes one or more components that minimize unwanted side-effects during injection of the composition.

V. Kits and Articles of Manufacture Comprising the Hyaluronan Compositions of the Invention Also within the scope of the present invention are kits comprising the HA compositions of the invention and instructions for use. The term "kit", as used herein, refers to a packaged product comprising components with which to administer the HA composition of the invention for treatment of a disease or disorder, e.g., joint pain. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering an HA composition of the invention.

The kit can further contain one more additional reagents and/or medications, such as non-steroidal anti-inflammatory drugs (NSAIDs) or nutritional supplements, e.g., supplements comprising glucosamine and/or chondroitin sulfates. Non-limiting examples of NSAIDS include aspirin, diflunisal, salsalate, choline magnesium trisalicylate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, melfenamic acid, meclofenamic acid, flufenamic acid, folfenamic acid, Celecoxib, Rofecoxib, Valdecoxib, Parecoxib, Lumiracoxib, Etoricoxib, Firocoxib, nimesulfide or licofelone. Kits typically include a label indicating the intended use of the contents of the kit. The term label includes any writing, or recorded material supplied on or with the kit, or which otherwise accompanies the kit.

The invention also provides a pharmaceutical pack or kit comprising one or more containers filled with a composition of the invention. In one embodiment, a container filled with a composition of the invention is a pre-filled syringe. In a specific embodiment, the compositions of the invention are formulated in single dose vials as a sterile liquid. Optionally associated with such container(s) can be a notice in the form prescribed by a governmental agency regulating the manufacture, use or sale of pharmaceuticals or biological products, which notice reflects approval by the agency of manufacture, use or sale for human administration.

In one embodiment, a container filled with a composition of the invention is a pre-filled syringe. Any pre-filled syringe known to one of skill in the art may be used in combination with a composition of the invention. Pre-filled syringes that may be used are described in, for example, but not limited to, PCT Publications WO05032627, WO08094984, WO9945985, WO03077976, U.S. Pat. Nos. 6,792,743, 5,607,400, 5,893,842, 7,081,107, 7,041,087, 5,989,227, 6,807,797, 6,142,976, 5,899,889, US Patent Publications US20070161961A1, US20050075611A1, US20070092487A1, US20040267194A1, US20060129108A1. Pre-filled syringes may be made of various materials. In one embodiment a pre-filled syringe is a glass syringe. In another embodiment a pre-filled syringe is a plastic syringe. One of skill in the art understands that the nature and/or quality of the materials used for manufacturing the syringe may influence the stability of an HA composition stored in the syringe. In one embodiment, a pre-filled syringe comprises a silicone based lubricant. In one embodiment, a pre-filled syringe comprises baked on silicone. In another embodiment, a pre-filled syringe is free from silicone based lubricants. One of skill in the art also understands that small amounts of contaminating elements leaching into the formulation from the syringe barrel, syringe tip cap, plunger or stopper may also influence stability of the composition. For example, it is understood that tungsten introduced during the manufacturing process may adversely affect formulation stability. In one embodiment, a pre-filled syringe may comprise tungsten at a level above 500 ppb. In another embodiment, a pre-filled syringe is a low tungsten syringe. In another embodiment, a pre-filled syringe may comprise tungsten at a level between about 500 ppb and about 10 ppb, between about 400 ppb and about 10 ppb, between about 300 ppb and about 10 ppb, between about 200 ppb and about 10 ppb, between about 100 ppb and about 10 ppb, between about 50 ppb and about 10 ppb, between about 25 ppb and about 10 ppb.

The present invention also encompasses a finished packaged and labeled pharmaceutical product. This article of manufacture includes the appropriate unit dosage form in an appropriate vessel or container such as a glass vial, pre-filled syringe or other container that is hermetically sealed. In one embodiment, the unit dosage form is provided as a sterile particulate free HA composition that is suitable for parenteral administration, e.g., injection into the knee or axial and appendicular joints.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question, as well as how and how frequently to administer the pharmaceutical. In other words, the article of manufacture includes instruction means indicating or suggesting a dosing regimen including, but not limited to, actual doses, monitoring procedures, and other monitoring information.

VI. Methods of Treatment Using the Hyaluronan Compositions of the Invention

The present invention also provides methods of treating, reducing or preventing at least one symptom associated with joint dysfunction. The methods include administering to a subject in need thereof a therapeutically effective amount of a composition of the invention, such that the at least one symptom associated with joint dysfunction is treated, reduced or prevented. In other embodiments, the present invention also provides methods for treating or preventing osteoarthritis, the methods including administering to a subject in need thereof a therapeutically effective amount of a composition of the invention, such that osteoarthritis is treated or prevented. In some embodiments, the present invention also provides methods for improving joint function.

A treatment or preventive effect is evident when there is a statistically significant improvement in one or more parameters of disease status or a pathological condition, e.g., at least one symptom associated with joint dysfunction, such as osteoarthritis pain. A treatment or preventive effect is also evident by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. The term "prevent" or "preventing", as used herein, comprises, e.g., prevention of re-occurrence of least one symptom associated with joint dysfunction, e.g., osteoarthritis pain, in a subject who has previously experienced the at least one symptom.

In some embodiments, the subject is a human, a mammal, e.g., a cat, a dog, a farm animal (such as a cow, a sheep, a horse, a donkey), or a rodent. In a specific embodiment, the subject is a human. In another specific embodiment, the subject is a horse, such as a race horse, or a dog.

In some embodiments, the "at least one symptom associated with joint dysfunction" may be caused, e.g., by a pathological condition. Non-limiting examples of such pathological conditions include osteoarthritis, rheumatoid arthritis, fibromyalgia, infection or inflammation of the joint. The at least one symptom associated with joint dysfunction may also be caused by a medical procedure, such as arthroscopy, orthoplasty, injury or long immobilization. In some embodiments, the at least one symptom associated with joint dysfunction is pain or reduced mobility of the joint.

As used herein, the term "reducing at least one symptom" comprises diminishing, ameliorating or eliminating at least one symptom associated with joint dysfunction, such as pain or reduced mobility. This term also comprises reducing the total number of movement-evoked nerve impulses, or reducing the mean number of impulses per movement, in intact or in inflamed joints after administering an HA composition of the invention. This term also comprises reducing the extent of the activation of ion channels, such as TRPV1 channels, that are involved in the process of pain transduction in neurons, upon administration of an HA composition of the invention. Activation of such channels may be measured, e.g., by measuring the change in intracellular $Ca^{2+}$ in neurons after a nociceptive impulse, or by measuring whole-cell currents in neurons, upon administering an HA composition of the invention. Furthermore, the term "reducing at least one symptom" also comprises diminishing nociceptive firing of neurons in an inflamed joints upon administration of an HA composition of the invention. In some embodiments, the HA compositions of the invention are more effective at reducing at least one symptom associated with joint dysfunction than other HA compositions, e.g., other HA compositions that are currently commercially available, such as Synvisc®. In some embodiments, HA compositions of the invention are able to reduce at least one symptom associated with joint dysfunction by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 96%, 97%, 98% or 99%.

In some embodiments, the methods of reducing at least one symptom associated with joint dysfunction comprise administering to a subject in need thereof a therapeutically effective amount of a composition of the invention. The term "therapeutically effective amount", as used herein, is intended to include an amount of an HA composition of the invention that, when administered to a subject in need thereof, is sufficient to treat, prevent or reduce at least one symptom associated with joint dysfunction or is sufficient to treat or prevent osteoarthritis. One of ordinary skill in the art, e.g., a physician, would be able to easily ascertain the amount of HA composition that would be therapeutically effective. In general, a therapeutically effective amount of the composition is between about 0.1 to about 500 mg, e.g., about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg.

In some embodiments, the therapeutically effective amount of an HA composition of the invention is sufficient to achieve an effective concentration of HA inside the knee joint, or in other axial or appendicular joints. Accordingly, the effective amount of HA is sufficient to achieve an intra-articular HA concentration of greater than 3%, e.g., 4%, 4.5%, 5%, 5.5%, 6%, 6.5%, 7%, 7.5%, 8%, 8.5%, 9%, 9.5%, 10%, or greater than 10%.

In carrying out the presently described methods, the compositions of the invention may be administered by any administration route determined to be suitable by one of ordinary skill in the art. In one embodiment, the compositions of the invention are administered by parenteral administration. In a specific embodiment, the HA compositions of the invention may be administered by an injection, e.g., by intra-articular injection. In some embodiments, a treatment regimen may comprise a single intra-articular injection. In other embodiments, a treatment regimen may comprise multiple intra-articular injections, e.g., 2, 3, 4, 5, 6 or more than 10 injections. One of skill in the art would be able to determine the appropriate treatment regimen and the timing for the HA compositions of the invention for each subject.

In some embodiments of the methods provided herein, the compositions will be administered as a single intra-articular injection or in multiple, e.g., 2, 3, 4, 5, 6 injections. In general, 2-6 mL of hyaluronan composition at a concentration of 4% will be administered. However, it should be appreciated that the volumes of composition administered may be of larger volume and/or higher concentration. Thus, in some embodiments, the volume of the composition of hyaluronan administered is at least 0.1 mL, at least 0.5 mL at least 1 mL at least 2 mL, at least 3 mL, at least 4 mL, at least 5 mL, at least 6 mL, at least 7 mL, at least 8 mL, at least 9 mL, at least 10 mL, at least 11 mL, at least 12 mL, at least 13 mL, at least 14 mL, at least 15 mL, at least 16 mL, at least 17 mL, at least 18 mL, at least 19 mL, at least 20 mL, at least 30 mL or more. In some embodiments, the composition of hyaluronan administered is between 1-30 mL, between 2-20 mL, between 2-10 mL, between 2-8 ml, between 3-6 mL, or between 4 and 5 mL.

In some embodiments, the volume of an HA composition of the invention administered to a subject is sufficient to fill a cavity in the subject's joint, e.g., the knee, elbow, hip or other appendicular or axial joint. The volume of the HA composition is also sufficient to coat the synovium in the subject's joint. In certain embodiments, the volume of the HA composition of the invention administered to a subject is sufficient to prevent dilution of the HA composition by the fluid inside the joint. For example, the volume of the HA composition of the invention is sufficient to maintain an HA concentration of 3% or greater, e.g., 4%, in the subject's joint.

In certain embodiments, the volume of the HA compositions of the invention administered to a subject in need thereof is sufficient for improving joint function, e.g., sufficient to reduce joint pain, yet, is sufficiently small, such as to prevent build-up of positive atmospheric pressure inside the joint.

In one aspect, the invention provides methods for improving joint function (e.g., knee, elbow, hip, shoulder joint, or other axial and appendicular joints). Improving joint function, as used herein, refers both to the improvement of the mechanical function (e.g., the ability to use the joint such as by, for instance, walking, running and the use of the hands), and the ability to reduce unwanted side effects (e.g., pain) associated with joint function. In one aspect, the disclosure provides a method of reducing pain associated with joint function. However, it should be appreciated that the improvement in joint function is not limited to improvement of the mechanical function and reduction of pain. Any improvement in joint function such as a reduction in inflammation or reduction in swelling is encompassed by the current methods.

In one aspect, the invention provides methods for treating osteoarthritis. Osteoarthritis (OA) is a degenerative joint disease characterized by a group of mechanical abnormalities involving degradation of joints including articular cartilage and subchondral bone. Symptoms associated with osteoarthritis include joint pain, tenderness, stiffness, locking. Osteoarthritis can affect any joint in the body. The most commonly affected joints are hands, feet, spine, hip and knee. Treating osteoarthritis, as used herein, refers both to the improvement of the mechanical function of the affected joint (e.g., the ability to use the joint such as by, for instance, walking, running and the use of the hands), and the ability to reduce the pain of the affected joint.

In one aspect, the present invention provides methods for improving mechanical joint function. In one aspect, the disclosure provides methods for improving the functionality of a joint affected with osteoarthritis. In one aspect, the methods for improving joint function and the functionality of a joint affected with osteoarthritis comprise introducing by injection into a joint a therapeutically effective amount of a composition of the invention, e.g., a composition comprising hyaluronan characterized by high elasticity. Improvement in joint function and improvement in the functionality can be evaluated relative to the functionality prior to treatment or compared to a subject who is not receiving the treatment. In some embodiments, improvement in functionality is measured by reference to a baseline of functionality experienced by the subject prior to being treated with the compositions provided herein. For example, in one embodiment, the subject may experience an improvement in functionality based on KOOS (Knee and Osteoarthritis Outcome Score) function in daily living (See, e.g., Roos et al., J. Orthop. Sports. Phys. Ther., (1998) 28:22-96).

In some embodiments of the methods provided herein, the subject may experience at least a 5, 10, 15, 20, 25, 30, 35, 40, 45, or 50 point change from baseline based on the KOOS function in daily living prior to receiving treatment. In some embodiments of the methods provided herein, the subject may experience at least a 5, 10, 15, 20, 25, 30, 35, 40, 45, or 50 point change from baseline based on the KOOS function in daily living compared to a subject not receiving treatment.

In some embodiments, the subject may experience an improvement in function measured by WOMAC (Western Ontario and MacMaster Universities Osteoarthritis Index) function subscale (see, e.g., Bellamy et al., Ann. Rheum.

Dis., (2005), 64:881-885). In some embodiments of the methods provided herein, the subject may experience at least a 20%, 30%, 40%, 50%, 60%, 70%, 80%, 90% or 100% improvement in function from baseline based on the WOMAC function subscale prior to receiving treatment. In some embodiments of the methods provided herein, the subject may experience at least a 20%, 30%, 40%, 50%, 60%, 70%, 80%, 90% or 100% improvement in function from baseline based on the WOMAC function subscale compared to a subject not receiving treatment.

In some embodiments, the improvement in joint functionality may be assessed using a questionnaire with the 5-point Likert scale.

In one aspect, the present invention provides a method of reducing pain associated with joint function. In another aspect, the present invention provides a method of reducing pain associated with osteoarthritis. In some embodiments, reduction of pain is measured by reference to a baseline of pain experienced by a subject prior to being treated with one of the compositions provided herein. For example, in some embodiments, the patient experiences a reduction of pain based on the commonly known KOOS (Knee and Osteoarthritis Outcome Score) pain subscale score which quantifies a subject's experience of pain based on a known range of factors (see, e.g., Roos et al., J. Orthop. Sports. Phys. Ther., (1998) 28:22-96). For example, in some embodiments, the subject may experience at least a 5, 10, 15, 20, 25, 30, 35, 40, 45, or 50 point change from baseline based on the KOOS pain subscale prior to treatment. In some embodiments, the subject may experience at least a 5, 10, 15, 20, 25, 30, 35, 40, 45, or 50 point change from baseline based on the KOOS pain subscale compared to a subject not receiving treatment.

In some embodiments, the subject may experience a reduction of pain measured by the WOMAC (Western Ontario and MacMaster Universities Osteoarthritis Index) pain subscale (see, e.g., Bellamy et al., Ann. Rheum. Dis., (2005), 64:881-885). For example, in some embodiments, the subject may experience at least a 20%, 30%, 40%, 50%, 60%, 70%, 80%, 90% or 100% reduction in pain from baseline based on the WOMAC pain subscale prior to treatment. In some embodiments, the subject may experience at least a 20%, 30%, 40%, 50%, 60%, 70%, 80%, 90% or 100% reduction in pain from baseline based on the WOMAC pain subscale compared to a subject not receiving treatment.

In some embodiments, the reduction of pain in a subject may be assessed using a questionnaire with the 5-point Likert scale.

A variety of treatment regimes are encompassed by the methods disclosed herein. For instance, a subject may receive a first dose of the hyaluronan compositions disclosed herein followed by additional doses. In some embodiments, a first dose is administered followed by a second dose at a specific interval. In some embodiments, the second dose is administered about 30 days, about 60 days, about 90 days, about 120 days, about 150 days, about 180 days, about 210 days, about 240 days, about 270 days, about 300 days, about 330 days, or about 360 days after the first dose. It should be appreciated that the dose regime may be adjusted based on the improvement in functionality and/or reduction in pain experienced by the subject. In some embodiments, the subject will receive a dose every month, every two months, every three months, every four months, every five months, every six months, every seven months, every eight months, every nine months, every ten months, every eleven months, or every twelve months. In some embodiments a dose is administered as a single or multiple intra-articular injection(s).

In one aspect, the compositions disclosed herein are administered directly to the pathological joints. For example, the compositions can be administered directly to a knee joint, hip joint, finger or thumb joint, toe joint, ankle joint, wrist joint, shoulder joint, elbow joint or joints of the spine. In some embodiments, the compositions are administered to a knee joint. In some embodiments, the compositions are administered to a shoulder joint. In some embodiments, the compositions are administered to a hip joint. In some embodiments the compositions are administered to a joint in the leg or arm. In some embodiments the compositions are administered to a joint in the leg or arm, other than a knee, shoulder or hip joint, or to an axial or appendicular joint. In some embodiments of any of the methods provided herein, the joint is a joint of the axial skeleton. In some embodiments of any of the methods provided herein, the joint is the temporomandibular or cranial joint.

In one aspect, the compositions are administered by introducing by injection into a joint a therapeutically effective amount of the composition. In some embodiments, the compositions are administered by intra-articular injection. In some embodiments, the compositions are administered via injection through a syringe and needle. In some embodiments, the compositions are administered topically at the site of the joint. In some embodiments, the compositions are administered periarticularly.

The present invention is further illustrated by the following Examples, which in no way should be construed as further limiting. The entire contents of all of the references (including literature references, issued patents, published patent applications, and co-pending patent applications) cited throughout this application are hereby expressly incorporated herein by reference.

EXAMPLES

Unless provided otherwise, the hyaluronan used in the compositions described herein is obtained from animal, human or bacterial sources. Unless provided otherwise, the compositions used herein are in physiological buffers.

Example 1

Elastic Properties of the HA Compositions of the Invention

The purpose of this experiment was to investigate the elastic properties of commercially available hyaluronan (HA) products of HA compositions of the invention. HA used in the preparation was obtained from bacterial cell wall source and had an average molecular weight of 1-2 million. The compositions were prepared in physiological saline (8.47 g/L NaCl) or a phosphate buffer solution (8.47 g/L NaCl, 0.047 g/L $NaH_2PO_4.H_2O$, 0.213 g/L $Na_2HPO_4$) with pH of 5.5-7.5. If samples were heat sterilized after preparation, the autoclave cycle used was either 121° C. for 15 minutes or 131° C. for 2 minutes with flash cooling of the material immediately following the cycle.

Measurements of the elastic properties of HA samples were conducted on a Stresstech High Resolution Research Rheometer from Reologica Instruments AB, Inc. using RheoExplorer software version 5.0.40.9. A frequency sweep oscillation test was performed and the elastic modulus (G') was determined. The frequencies of interest range from 0.1 to 10 Hertz (Hz or cycles/sec) which correspond to the degree of movement or stress in the human knee joint during standing, walking, running and jumping.

Table 1 below shows HA concentration and average molecular weight in selected HA commercial products for viscosupplementation.

TABLE 1

HA Concentrations and Average Molecular Weights for Commercial HA Products

| Product | Manufacturer | Average MW of HA | Concentration of HA |
|---|---|---|---|
| Synvisc ® | Sanofi | 5 million | 0.8% (8 mg/mL) |
| Synvisc ® One | Sanofi | 5 million | 0.8% (8 mg/mL) |
| Euflexxa ® | Ferring Pharmaceuticals | 3 million | 1% (10 mg/mL) |
| Supartz ® | Seikagaku Corp. | 1 million | 1% (10 mg/mL) |
| Gel-One ® | Seikagaku Corp. | 1 million (before cross-linking) | 1% (10 mg/mL) |
| Hyalgan ® | Fidia Pharma | 0.6 million | 1% (10 mg/mL) |
| Orthovisc ® | Anika Therapeutics, Inc. | 2 million | 1.5% (15 mg/mL) |
| Monovisc ® | Anika Therapeutics, Inc. | 1-2.9 million | 2.2% (22 mg/mL) |
| Synocrom ® | Chroma-Pharma GmbH. | 1.6 million | 1% (10 mg/mL) |
| Synocrom ® Mini | Chroma-Pharma GmbH | 1.6 million | 1% (10 mg/mL) |
| Synocrom ® Forte | Chroma-Pharma GmbH | 2.1 million | 2% (20 mg/mL) |
| Synocrom ® Forte One | Chroma-Pharma GmbH | 2.1 million | 2% (20 mg/mL) |
| Synolis V-A | Anteis | 2 million | 2% (20 mg/mL) |

The elastic properties of selected commercially available HA products for viscosupplementation were evaluated by measuring the elastic modulus (G') over frequencies ranging from 0.1 to 10 Hertz (Hz or cycles/sec). Joints operate at frequencies ranging from 0.1 to 7 Hz, with frequencies determining the force that the joint surfaces experience in standing up, walking, running and jumping. The elastic behavior of HA in this frequency range determines the transmission of mechanical forces to both joint surfaces in the knee joint. Table 2 below shows the measured values of G' (in Pascal) at various frequencies in five HA commercial products, and FIG. 1, Panel A shows the same data in a graph format.

TABLE 2

G'Values (in Pascal) for HA Commercial Products

| Frequency (Hz) | Orthovisc ® | Synvisc ® | Euflexxa ® | Supartz ® | Hyalgan ® |
|---|---|---|---|---|---|
| 7 | 188 | 131 | 117 | 30 | 6 |
| 5 | 170 | 125 | 109 | 10 | 12 |
| 2 | 156 | 120 | 103 | 21 | 2.0 |
| 1 | 117 | 106 | 84 | 10 | 0.5 |
| 0.5 | 64 | 80 | 56 | 2 | 0.08 |
| 0.1 | 22 | 49 | 30 | NA | NA |

Table 3 below shows the measured values of G' (in Pascal) at various frequencies in several inventive compositions, and FIG. 1, Panel B shows the same data in a graph format.

TABLE 3

G'Values (in Pascal) for Compositions of the Invention

| | HA Concentration | | | | |
|---|---|---|---|---|---|
| Frequency (Hz) | 2.0% | 3.5% | 4.5% | 6.5% | 8.9% |
| 7 | 423 | 1,020 | 2,142 | 4,898 | 6,920 |
| 5 | 394 | 957 | 2,003 | 4,623 | 6,530 |
| 2 | 315 | 788 | 1,691 | 4,029 | 5,850 |
| 1 | 232 | 604 | 1,356 | 3,376 | 5,010 |
| 0.7 | 193 | 515 | 1,189 | 3,021 | 4,550 |

TABLE 3-continued

G'Values (in Pascal) for Compositions of the Invention

| | HA Concentration | | | | |
|---|---|---|---|---|---|
| Frequency (Hz) | 2.0% | 3.5% | 4.5% | 6.5% | 8.9% |
| 0.5 | 157 | 435 | 1,025 | 2,678 | 4,110 |
| 0.1 | 54 | 168 | 459 | 1,368 | 2,290 |

Table 4 below shows comparison of G' values for selected HA commercial products and selected HA compositions of the invention.

TABLE 4

Comparison of G'values at different frequencies for HA commercial products and HA compositions of the invention

| | Walking, 0.5 Hz | Running, 2.5 Hz | Jumping, 5 Hz |
|---|---|---|---|
| HA Commercial Products | | | |
| Orthovisc ® | 64 | 160 | 170 |
| Synvisc ® | 80 | 125 | 125 |
| Euflexxa ® | 56 | 110 | 109 |
| Supartz ® | 2 | 22 | 10 |
| Hyalgan ® | 0.08 | 3 | 2 |
| Inventive Compositions HA concentration | | | |
| 3.5% | 433 | 800 | 957 |
| 4.5% | 1,025 | 1,700 | 2,005 |
| 6.5% | 2,678 | 4,100 | 4,600 |
| 8.9% | 4,110 | 6,000 | 6,530 |

As can be seen from the data, the compositions of the invention are characterized by much higher G' values than any of the tested HA commercial products. The G' values of HA compositions reflect the ability of HA molecules to act as a coiled molecular shock absorber and behave like an elastic solid.

Example 2

In Vivo Analgesic Effects of the HA Compositions of the Invention

Thin nerve filaments from the saphenous nerve of adult male Wistar rats were dissected and placed on a silver wire electrode and nerve impulses in pain nerve fibers evoked by mechanical stimulation were assessed. Joints were rotated to replicate innocuous movement (within the working range of the joint) and noxious movement (exceeding the working range of the joint). Rotations that included an innocuous movement followed by a noxious movement, i.e., a movement cycle, were repeated every 5 minutes for the duration of the experiment. The nerve activity was analyzed by separately counting the number of nerve impulses during the innocuous and during the noxious components of each individual movement cycle. The numbers of nerve impulses evoked by each component (non-noxious and noxious) were summed to obtain the total number of impulses of the movement cycle at each time point.

The experiment was conducted to test the analgesic effects of compositions containing HA of different average molecular weights (from 0.2 to 6 million) and increasing concentrations (from 1% to 6%) on joint pain receptors of intact and inflamed joints. In a group of experiments, kaolin-carrageenan was injected intra-articularly into joints to induce joint inflammation. One hour later, HA solutions of different concentrations and average molecular weight or saline control were injected intra-articularly, and the time course of the analgesic effect was determined. The analgesic effect was assessed by measuring impulses in pain joint nerve fibers during 8 hours following the intra-articular injection of the test substance.

Figure 2:
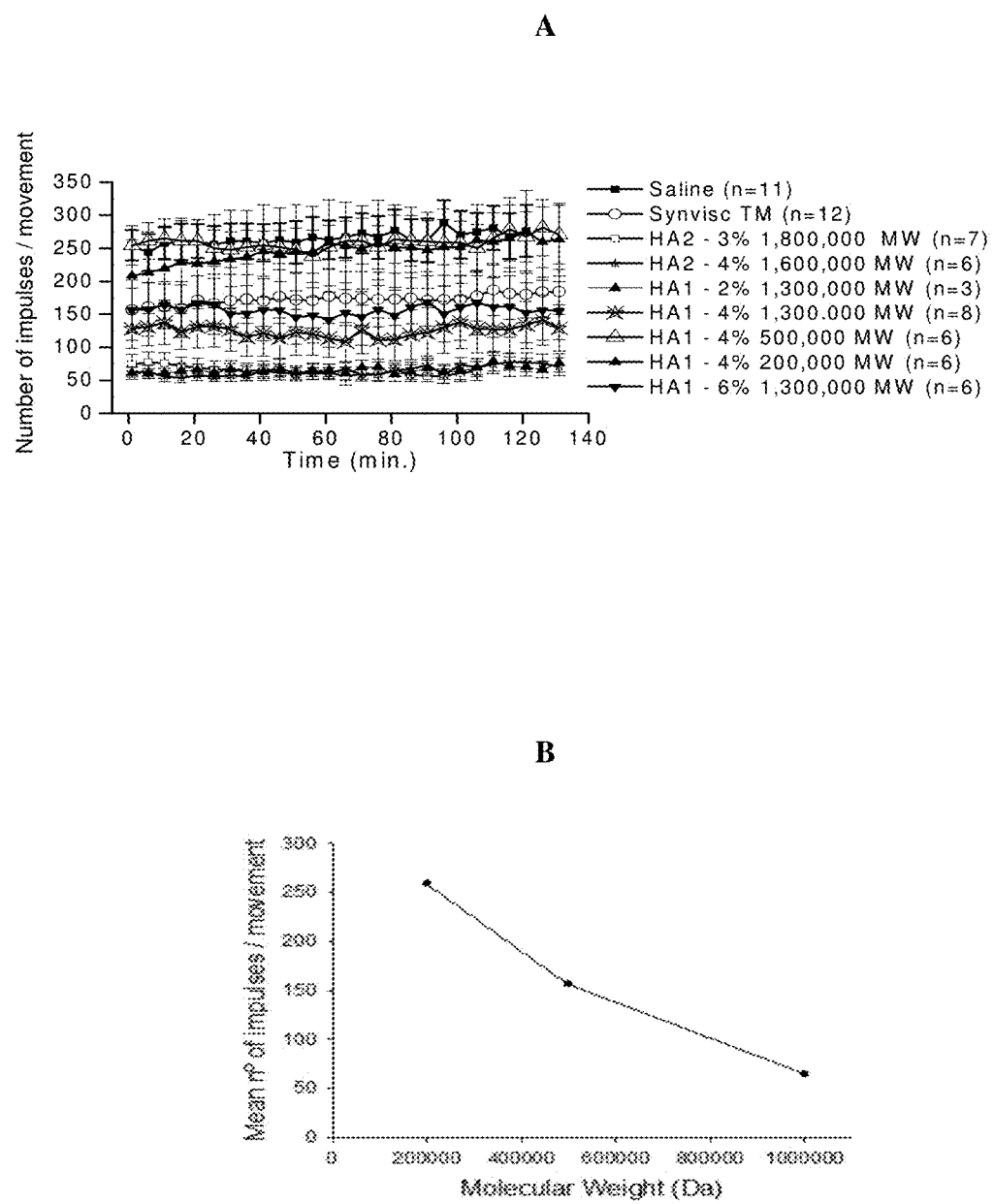
FIG. 2, Panel A is a graph showing the number of nerve impulses per movement in inflamed joints as a function of time after injection of Synvisc® and various HA compositions of the invention.
Figure 2:
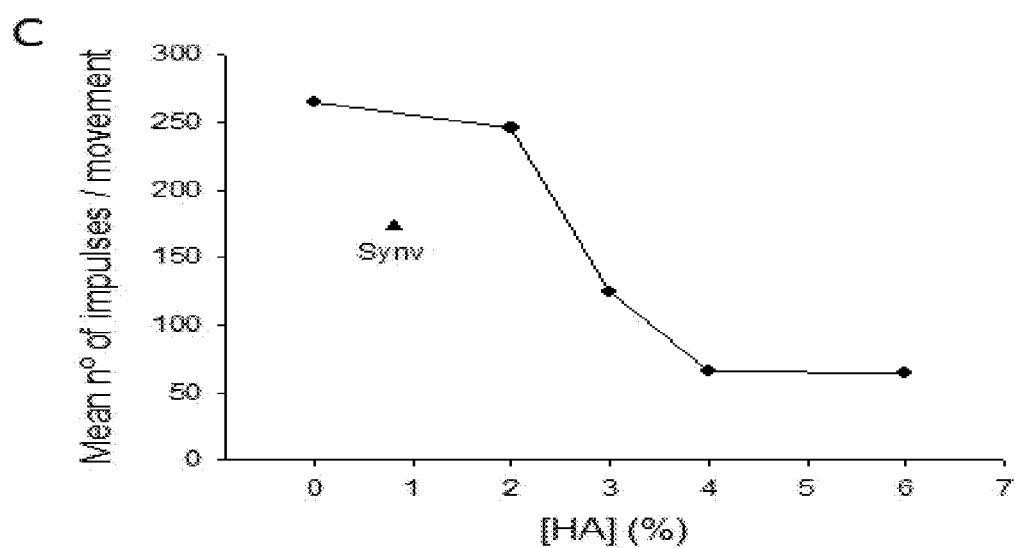
Figure 2:
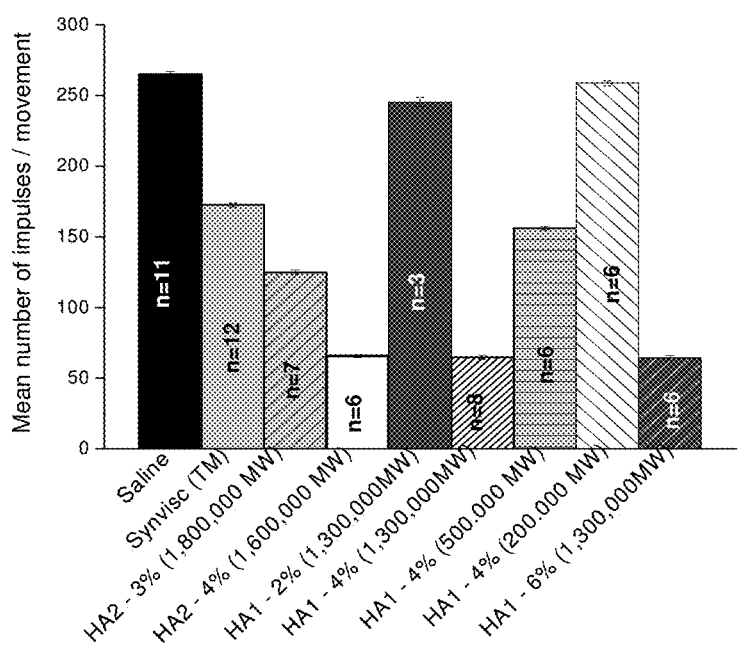

FIG. 2 summarizes the results. Shown in Panel A is the average number of impulses per movement evoked by a complete movement cycle repeated every 5 min. The impulses were measured in single fibers of the median articular nerve of inflamed joints treated for 24 hours with the compositions of different HA concentrations and average molecular weights, as indicated in the right inset. It is clear that solutions containing HA of an average MW of 1.3-1.6 million or greater and at concentrations of 4% or greater are most effective in reducing the number of nerve impulses evoked by successive movement cycles. Panel B shows the mean number of impulses per movement as a function of the average molecular weight for 4% HA compositions. The results demonstrate higher efficacy of compositions having the average molecular weight of 1 million or greater. Panel C shows the mean number of impulses per movement as a function of HA concentration. The results evidence maximal effects obtained with 4% HA compositions. The effect of Synvisc® injection is marked by the black triangle. Panel D shows the summary of the mean effects on movement-evoked activity in inflamed knee joints 24 hours after treatment with HA compositions of different concentrations and average molecular weights. HA2 corresponds to HA of the average molecular weight of 1.3 million, provided by Croma-Pharma GmbH. HA1 corresponds to the HA composition provided by the Matrix Biology Institute.

The results presented in FIG. 2 demonstrate that 4% HA compositions with the average molecular weight of 1 million are very effective at reducing the mean number of nerve impulses in the inflamed joints and is therefore effective at reducing pain in the inflamed joints.

Accordingly, pain nerve impulse activity evoked by movement in inflamed joints is high and remains stable through the recording period. Injection of 4%-6% HA, with average MW of 1.3 million or over had a pronounced inhibitory effect on the movement-evoked impulse activity. A similar reduction was obtained with 6% HA MW of 1.6 million. Reduction of the concentration of HA maintaining constant the MW or employing 4% HA solution of lower MW reduced the inhibitory effect. Results obtained with the commercial HA solution Synvisc®, which contains 0.8% HA with a MW around 6 million has been also represented for comparison. It can be safely concluded that HA of an average MW over 1.3 million exerts a powerful inhibitory effect on movement-evoked joint nociceptor activity.

Figure 3:
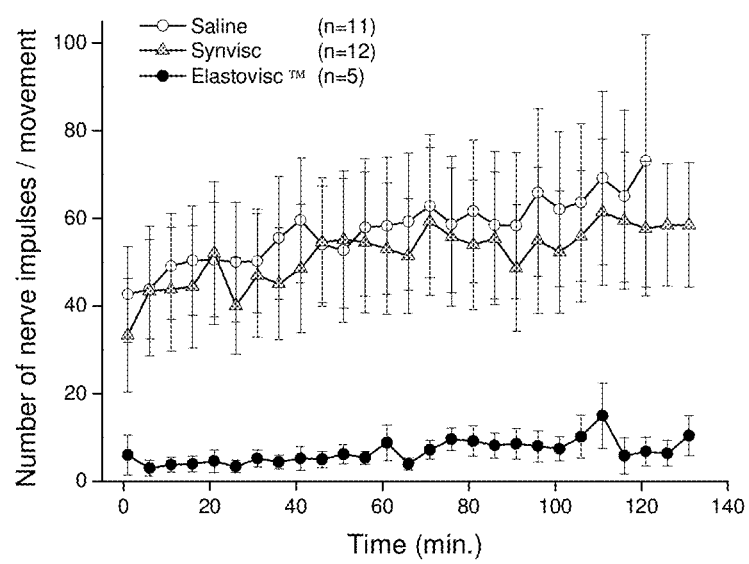
FIG. 3, is a graph showing the number of nerve impulses evoked by the non-noxious component of the joint movement cycle as a function of time measured in inflamed rat joints following injection with saline solution, Synvisc® or HA composition of the invention (Elastovisc™, 4% HA, average molecular weight 1-2 million).
Figure 4:
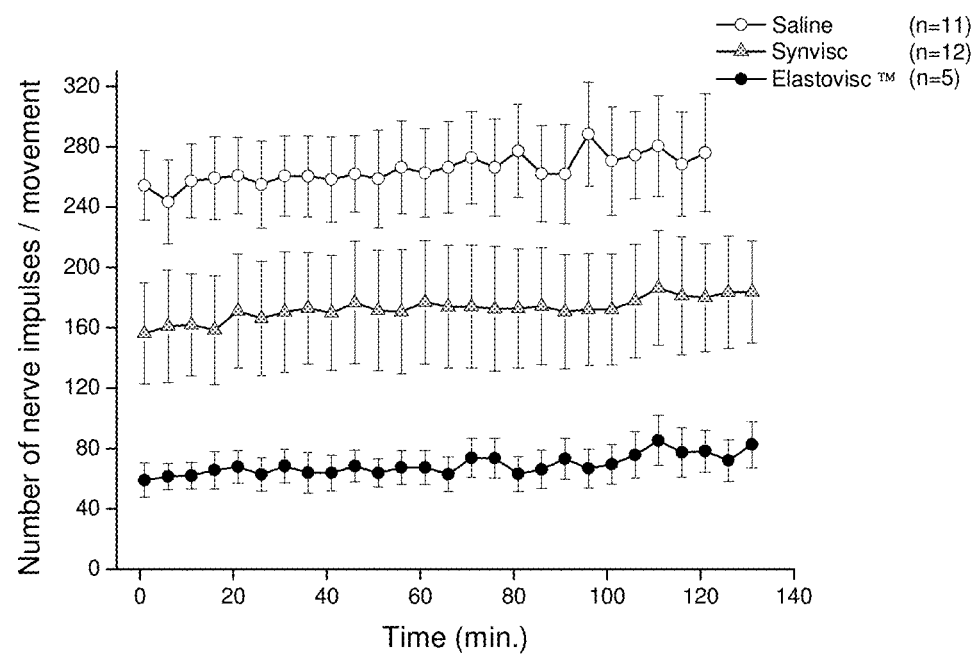
FIG. 4 is a graph showing the number of nerve impulses evoked by the noxious component of the movement cycle as a function of time measured in inflamed rat joints following injection with saline solution, Synvisc® or HA composition of the invention (Elastovisc™, 4% HA, average molecular weight 1-2 million).

FIGS. 3 and 4 show that the 4% HA composition affects both the nerve impulse activity evoked by the innocuous and by the noxious components of the movement cycle. FIG. 3 represents the number of nerve impulses counted during the non-noxious part of the movement in inflamed joints that had been injected 24 hour prior with saline, 4% HA or Synvisc®. FIG. 4 shows the data corresponding to the noxious part of the movement cycle. These results confirm the efficacy of the 4% HA composition in reducing the overall responsiveness of joint pain nerve fibers to movement-evoked pain activity.

Figure 5:
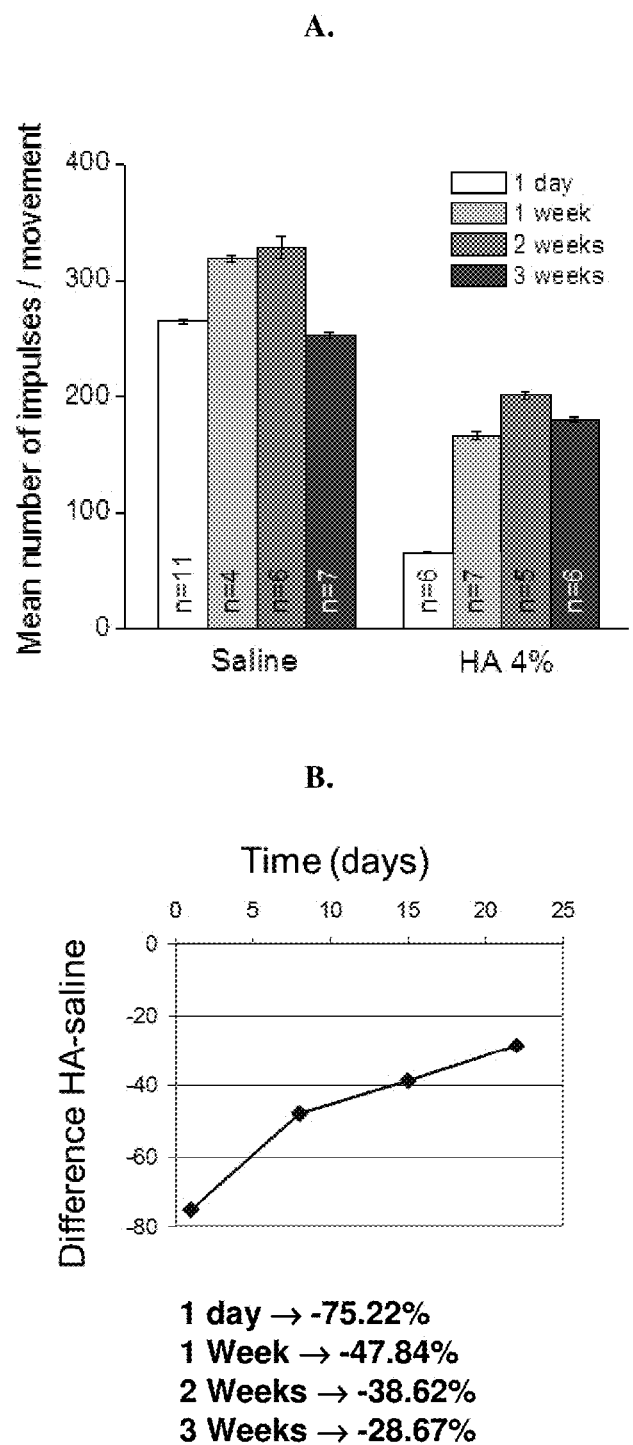
FIG. 5, Panel A shows the average total number of impulses per movement recorded at different times after the onset of inflammation followed by an intra-articular injection of saline or a 4% HA composition of the invention.

FIG. 5 shows long-term effects of the intra-articular injection of 4% HA composition on nerve impulse activity. Panel A shows the average number of impulses per movement recorded at one day, one week, two weeks and three weeks after the onset inflammation, followed by an intra-articular injection of saline or 4% HA composition. Panel B shows percent difference in the mean number of impulse/movement measured after saline injection and 4% HA, at the same time points as in Panel A.

Figure 6:
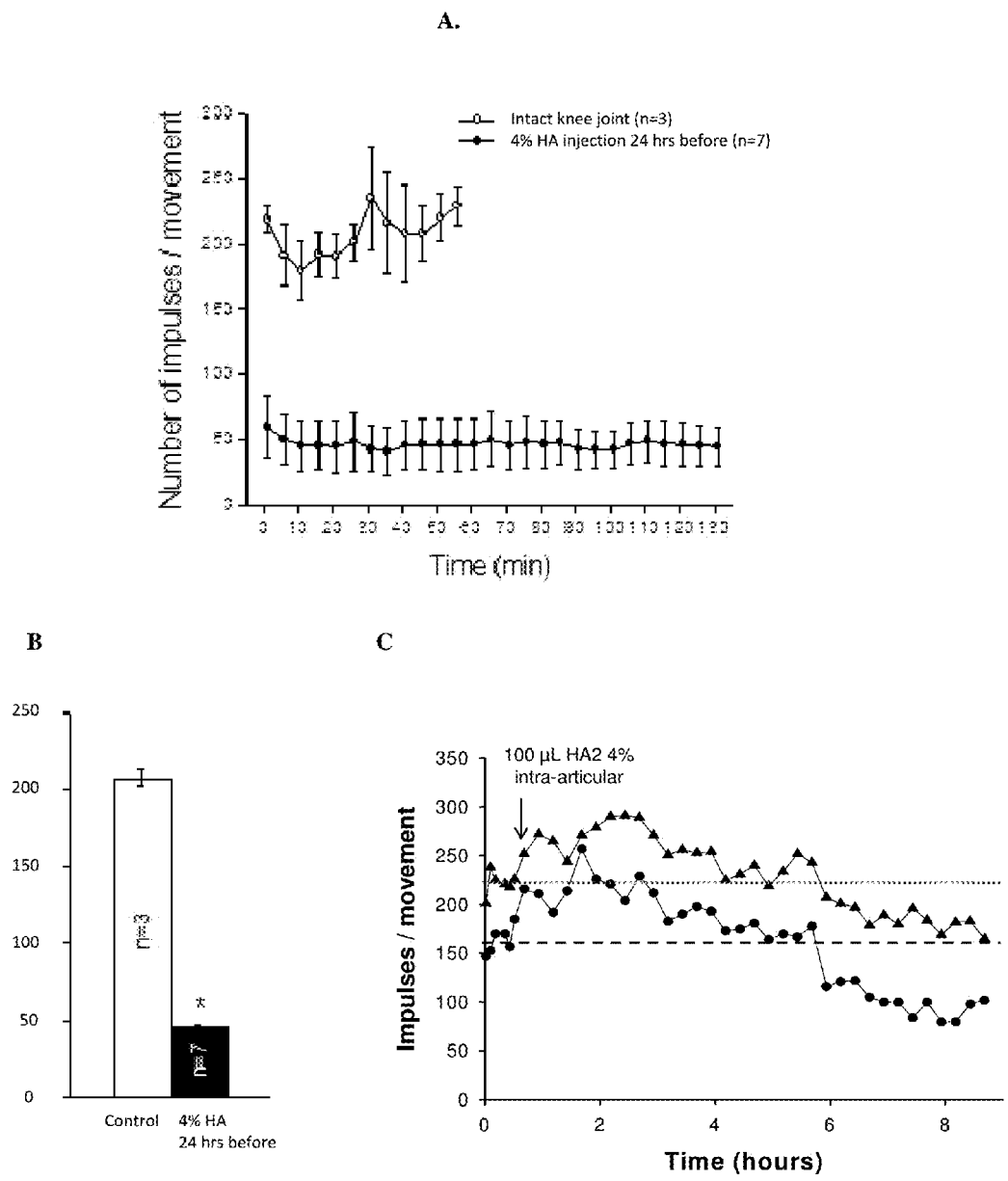
FIG. 6, Panel A is a graph showing the mean number of impulses per movement with repeated movements in three un-injected intact joints (open circles) and in seven intact joints (filled circles) following an intra-articular injection of 4% HA composition of the invention 24 hours earlier.

The inhibitory effect of HA 4% on movement-evoked activity was also observed in intact joints. As is shown in FIG. 6, Panel A, the total number of movement-evoked impulses in intact animals was around 210 impulses per cycle as shown by the data of the upper curve (open circles). When the same recording was made in intact animals 24 hours after injection of 4% HA, the mean number of impulses evoked by the same movement was very low, below 50 impulses per cycle. This is shown in FIG. 6, lower curve (filled circles) and Panel B, showing the average data of 7 experiments. This demonstrates that the effects of HA on joint nociceptors are also present in the non-sensitized fibers.

To determine the time point at which the inhibitory effect of HA starts to develop, the activity evoked by joint movement in two intact rats was recorded. After performing 6 movements at 10 min intervals, 4% HA composition (Elastovisc™) was injected intra-articularly. Movements were repeated with the same time interval during the following 8 hours. As is shown in FIG. 6, Panel C, in two individual fibers, the movement-evoked activity augmented gradually during the first 30-60 minutes after injection and then started to decline. Control values were recovered around 3 hours of the injection and decreased gradually during the next 2 to 3 hours, at which point the experiment was interrupted.

Figure 7:
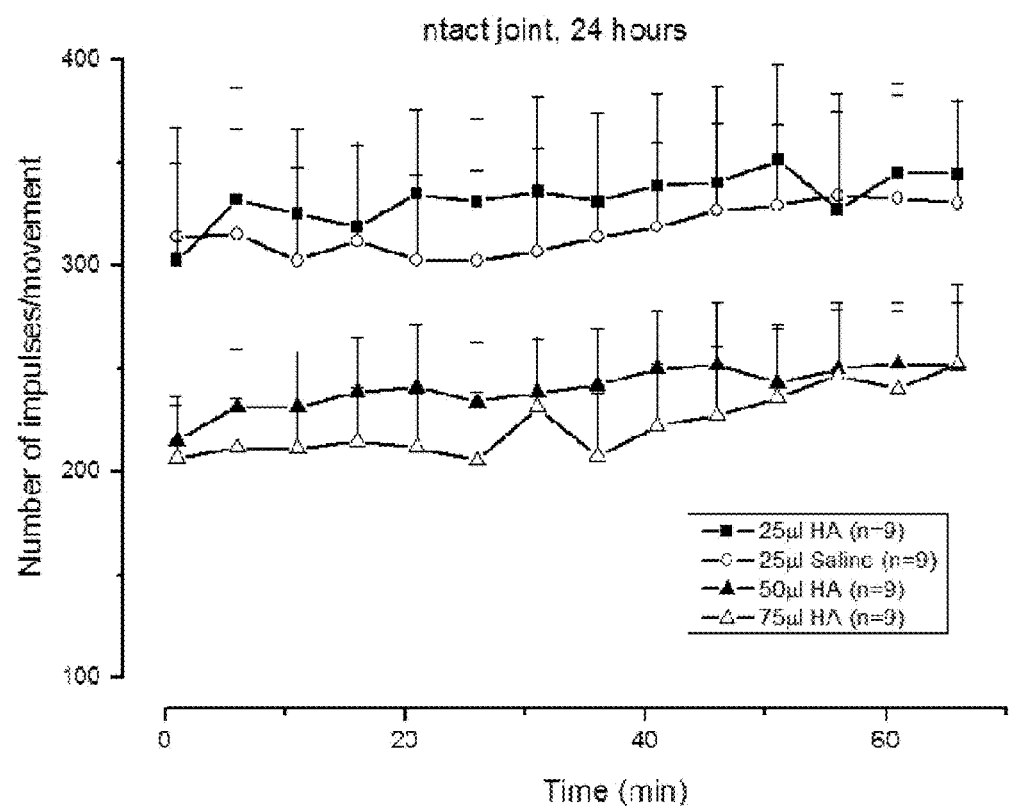
FIG. 7 is a graph showing the number of movement-evoked nerve impulses as a function of time measured in intact rat joints following intra-articular injection with saline or three different volumes of the HA composition of the invention (Elastovisc™).

FIG. 7 shows that the inhibitory effect of HA on movement-evoked activity is dependent on the total volume of HA injected intra-articularly in intact joints. When the injection volume is 25 μl, the curve representing movement evoked impulse activity (black squares) is similar to the one obtained with intra-articular saline (open circles). With 50 μl (black triangles) and 75 µl (open triangles), the movement-evoked activity in pain fibers was significantly lower than in control.

Example 3

In Vitro Effects of HA Compositions of the Invention on Ion Channels Involved in Pain Transduction The rheological properties of extracellular HA determine the effectiveness of HA in filtering the transmission of mechanical energy to pain nerve endings in the joint, and are affected by the local inflammatory or degenerative processes. In addition, during injury and inflammation, a large variety of locally released chemical mediators act on peripheral nociceptor endings causing sensitization. However, the possibility exists that the attenuating effect of HA on pain is also due to a modification of the transduction and excitation mechanisms activated by injury in peripheral nociceptors. This modification would be associated to the concentration and size of HA molecules.

Transient Receptor Potential Cation Channel Subfamily V Member 1 (TRPV1) is a non-selective cationic channel that plays a major role in the detection of noxious stimuli and in the sensitizing effects of inflammatory mediators on nociceptive nerve endings. TRPV1 behaves as an integrator of noxious endogenous and exogenous chemical and thermal stimuli in polymodal nociceptor terminals. In joints, TRPV1 has been implicated in the inflammatory effects caused by mediators released during long-term systemic painful arthritis.

The purpose of this experiment was to investigate the effect of HA on the activation of TRPV1, the main ion channel involved in pain transduction. Two cell lines were used for the experiments: the cell line SH-SY5Y VR1 that was genetically modified to have an increased expression of TRPV1, and HEK293 cells transfected with the TRPV1+ EYFP fusion protein to induce TRPV1 channel expression and identify visually the cells containing the TRPV1 channels. It is well established that heat and capsaicin selectively open the TRPV1 channels, allowing the entrance of calcium ($[Ca^{2+}]$) into the cells, which can be measured using optical imaging techniques. Accordingly, excitation of the cells corresponds to a transient increase in specific cell fluorescence that was registered and measured quantitatively. Change in intracellular calcium concentration caused by the opening of TRPV1 channels in response to natural noxious stimuli was measured in individual cells. After loading the cells with a fluorescent calcium probe (Fura-2AM), the cells were stimulated four times with short heat pulses and the change in calcium ions was measured. To define a reliable response to repeated stimuli with heat excluding tachyphylaxis (i.e., reduction of the response to repeated stimuli) the characteristics of the response of TRPV1 cells to repeated stimuli was defined. Rapid heating pulses of the cell surface up to 47-48° C. were used as the noxious stimulus, applied for 30 seconds and repeated at 10 minute intervals (see the example shown FIG. 8, panel A1). To quantify the effect of the stimulus, the change in intracellular calcium ($[Ca^{2+}]_i$) occurring under controlled conditions in response to an initial heating pulse in each cell was measured, and the response was averaged for a large number of cells. A protocol of repeated stimuli at fixed time intervals was established thereafter. The 4th pulse was considered the most stable and the percent reduction of its amplitude, in comparison with the amplitude of the first stimulus (taken as a baseline reading of 100%), was considered to be due to the effect of tachyphylaxis. Hence, the response of the cells to the 4$^{th}$ pulse was expressed in terms of the percent reduction in the magnitude of the first response when perfused with the control solution.

The effects of HA on TRPV1 channels expressed by fluorescent cultured HEK293 cells transfected with the TRPV1+ EYFP fusion protein to induce TRPV1 channel expression, and by dissociated dorsal root ganglion (DRG) primary sensory neurons were investigated by measuring the change in intracellular calcium $[Ca^{2+}]_i$ evoked by repeated noxious stimuli (heat or application of the TRPV1 agonist capsaicin) before and after perfusion with HA. HA compositions of an average MW of 5.6 million were used for these studies and were prepared to obtain a final solution containing 400 µg/ml of HA.

Figure 8:
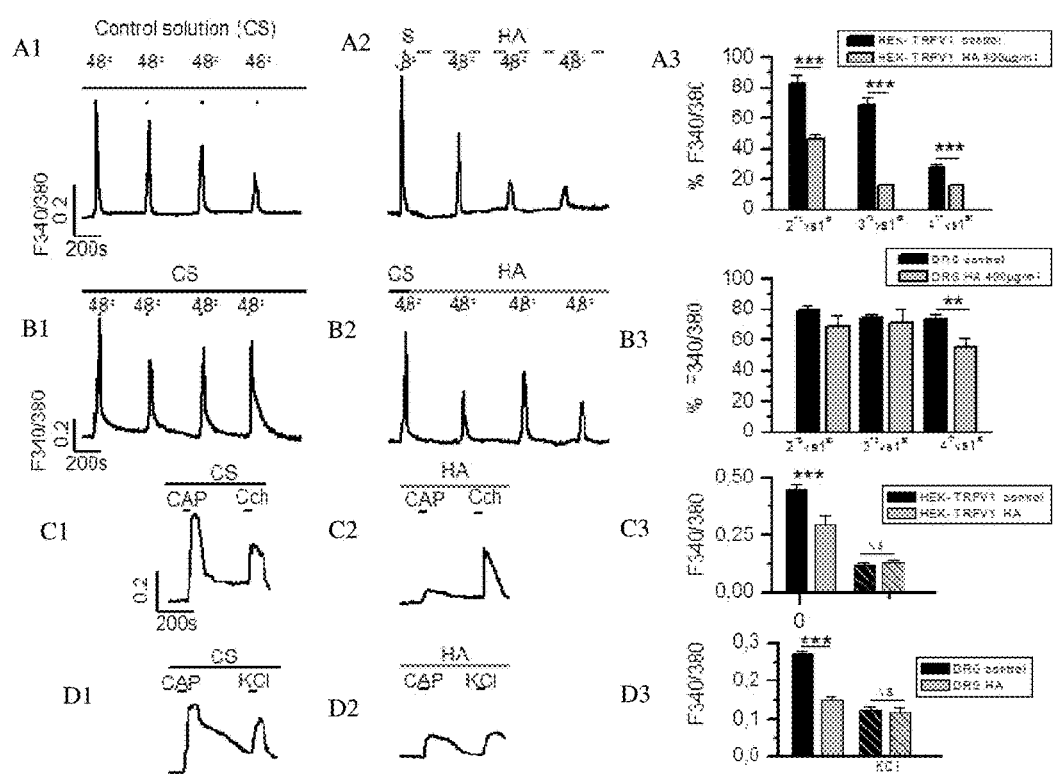
FIG. 8, Panels A1 and A2 show intracellular calcium rises evoked in HEK-TRPV1-EYFP(+) cells by heat after perfusion with saline (A1) or 400 μg/mL HA (A2). Panel A3 shows the ratio of average amplitude change between responses evoked by successive heat pulses in control saline solution and during perfusion with HA for HEK-TRPV1-EYFP(+) cells.

The results of the experiment are shown in FIG. 8. Panel A1 shows intracellular calcium rises evoked in HEK-TRPV1-EYFP (+) cells by heating the bathing solution to 48° C., repeated at 10 min intervals. Cytosolic $Ca^{2+}$ increases are represented as the ratio of the emission fluorescence intensities at 340 and 380 nm (F340/380: fluorescence arbitrary units). Panel A2 shows the same experiment as in A1, but with 400 µg/ml HA perfusion started at the end of the 1st heating stimulus. Panel A3 shows the ratio of average amplitude change between responses evoked by successive heat pulses (indicated in the abscissae axis) in control saline solution (CS, black bars) and during perfusion with HA (gray, bars). It is notable that inhibition appears 20 min after the onset of the HA perfusion.

Panels B1-B3 show the results of an experiment utilizing the same protocol as in A1-A3 but performed in the DRG adult neurons. The inhibitory effect of HA becomes evident after 30 minutes of treatment (see 4th vs 1st stimuli).

Panels C1-C3 show intracellular calcium change in a HEK-TRPV1-EYFP (+) cell in response to 100 nM capsaicin and 10 µM Carbachol (Cch), in control saline solution (C1) and under exposure to HA initiated 30 min earlier (C2). Panel C3 shows average amplitude of the response to capsaicin (filled bars) and Carbachol (striped bars) under perfusion with control saline solution (black) and in the presence of HA (gray).

Panels D1-D2 show intracellular calcium responses of DRG adult sensory neurons to 100 nM capsaicin and 30 mM KCl during perfusion with saline (D1) and with HA (D2). Panel D3 shows the average amplitude of the intracellular calcium responses to capsaicin (filled bars) or KCl (striped bars) in control saline solution (black) and in presence of HA (gray).

The results in FIG. 8 demonstrate that after a 30 minute exposure to HA, the response of cultured HEK-TRPV1 cells to heat pulses was reduced by 77% as compared to the control cells perfused with saline. In the experiment utilizing an identical protocol, the response of cultured DRG neurons to heat pulses was reduced by 24% as compared to the control. Also, a significantly lower number of HEK-TRPV1 cells (63%) responded with an intracellular calcium increase after stimulation with 100 nM capsaicin in the presence of HA, with the amplitude of the response being 33% lower as compared to the control conditions. Likewise, 68% of DRG neurons perfused with saline responded to capsaicin, while only 37% of DRG neurons perfused with HA responded, with the amplitude of the response reduced to 44% of control. Accordingly, by reducing the excitability of neurons, HA can effectively reduce pain.

Another cell line, the SH-SY5Y VR1 was used for experiments where the effect of the concentration of HA on the responses to heat of TRPV1 was studied. Table 5 shows the effect of Low- and High MW HA on the intracellular calcium response to heat in SH-SY5Y VR1 cells. Values of the response to the $4^{th}$ heating pulse are expressed as % of the response to the first pulse, under perfusion with saline (control) and with Low MW HA (average MW 470000 Da) or High MW HA ($5.2 \times 10^6$ Da) at concentrations of 200, 400 and 800 μg/ml (n=total number of cells measured in different experiments for each concentration; t-student statistics *P<0.05, 0.01<P<0.001, *P<0.001). As shown in Table 5, when higher concentration HA solutions of low (600000) or high (5.6M) MW were applied to SH-SY5Y VR1 cells, their response to heat was significantly diminished.

TABLE 5

Effect of Low- and High MW HA on the Intracellular Calcium Response to Heat in SH-SY5Y VR1 cells.

| Control | LMW | HMW |
|---|---|---|
| 51.8 ± 1.6 (n = 510) | 200 = 45.3 ± 1.6 (n = 472) * | 200 = 22.6 ± 1.2 (n = 353) *** |
| 53.7 ± 0.9 (n = 1119) | 400 = 33.7 ± 0.6 (n = 1025) *** | 400 = 17.9 ± 0.8 (n = 400)*** |
| 62.2 ± 1.6 (n = 267) | 800 = 32.0 ± 0.5 (n = 765)*** | 800 = 16.7 ± 0.6 (n = 192)*** |

Example 4

Figure 9:
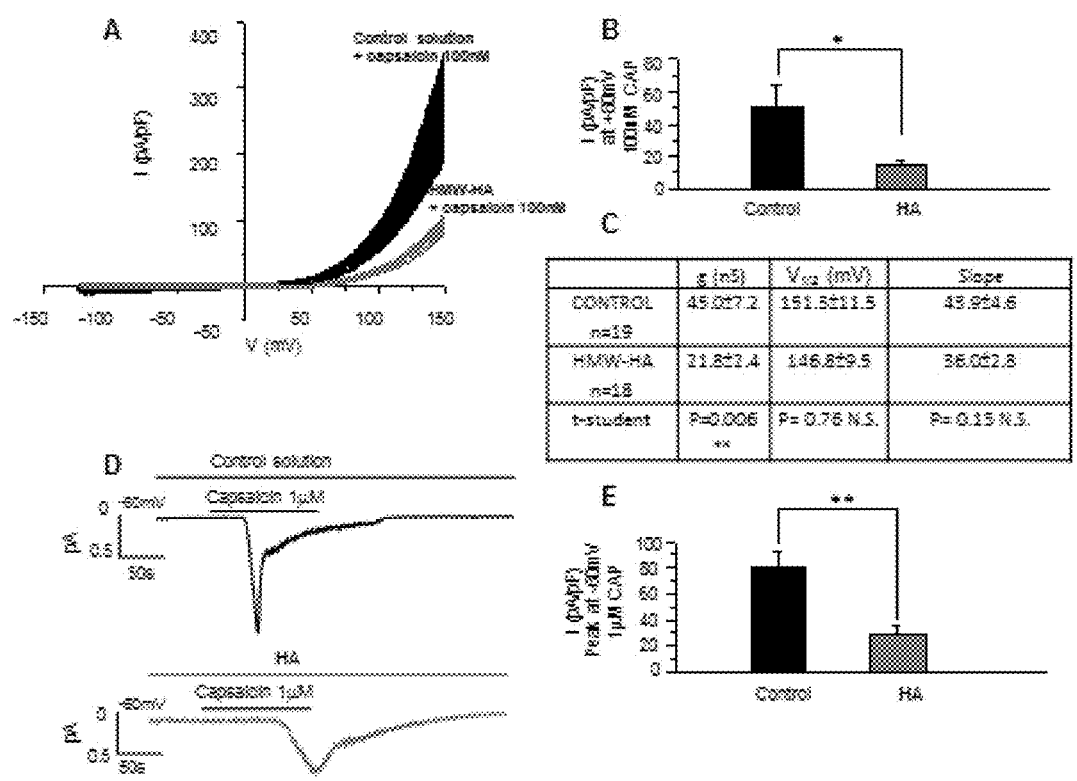
FIG. 9, Panel A shows I-V relationships of capsaicin-evoked currents in HEK-293-TRPV1 cells in saline solution (black trace) and in the 400 μg/ml HA solution (gray trace).

In Vitro Inhibition of Neuronal Excitability by the HA Compositions of the Invention HA-mediated inhibition of capsaicin-evoked stimulation of HEK-TRPV1 cells was also investigated by recording whole-cell currents in HEK-293-TRPV1-EGFP(+) cells. Shown in FIG. 9, Panel A are I-V relationships of TRPV1 activated with 100 nM capsaicin in saline solution (top trace, average of n=19) and in the 400 μg/ml HA solution (bottom trace, average of n=18). Voltage ramps were −120 mV to +10 mV, 0.2 Hz, with a slope of 0.8 mV/ms mV/s measured at a voltage of +80 mV. FIG. 9, Panel B shows the average current at +80 mV obtained from the I-V curves shown in Panel A. FIG. 9, Panel C shows values of different parameters measured from the ramps fitted with a function that combines a linear conductance multiplied by a Boltzmann activation term, $I = g \times (V - E_{rev})/(1 + \exp((V_{1/2} - V)/S))$. FIG. 9, Panel D shows whole-cell currents now at −60 mV in response to 1 μM capsaicin, in control conditions (top trace), and in cells pre-incubated for 30 minutes and continuously perfused with HA (bottom trace). FIG. 9, Panel E shows average values of peak currents evoked by capsaicin at −60 mV in saline and in the presence of HA.

The results presented in FIG. 9 demonstrate that capsaicin evokes membrane currents in HEK-TRPV1 cells and in DRG neurons mediated by TRPV1. The maximum amplitude of the current flowing through TRPV1 channels and recorded with the patch-clamp technique in response to capsaicin was reduced by 72% after exposure to HA. This inhibitory effect was still present at physiological values of −60 mV of the membrane potential of the cells. It was also confirmed that the voltage gating mechanism and voltage dependence of TRPV1 was not affected by HA, although the conductance (g) was reduced by 47%.

Modulation of TRPV1 single-channel activity by HA was also investigated. The observed decrease in macroscopic currents caused by HA on HEK-TRPV1 cells was explored by measuring single-channel currents before and after 30-60 min exposure to HA. The single channel activity evoked by 0.25 μM capsaicin present in the pipette was recorded in cell-attached patches of HEK293-TRPV1-EFYP (+) cells. The recordings were performed at +60 mV.

Figure 10:
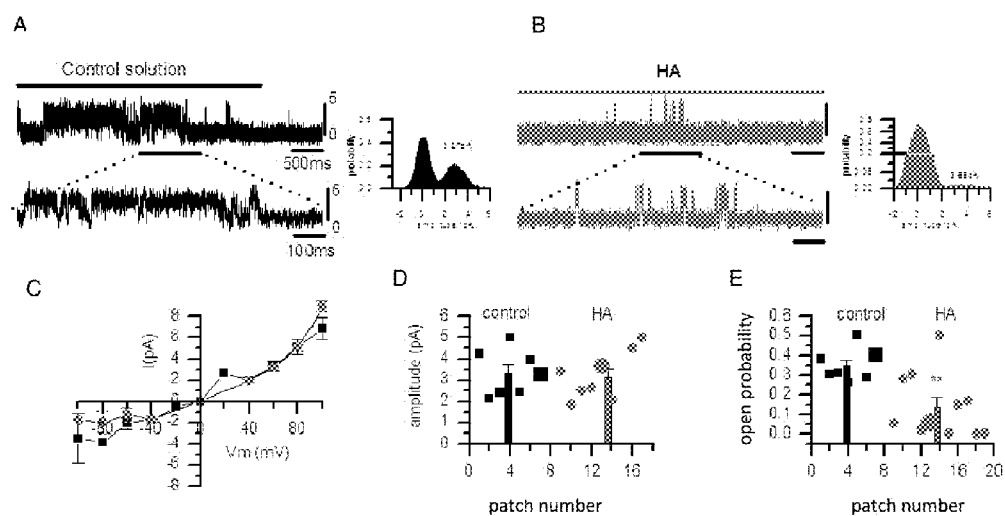
FIG. 10, Panel A shows a sample record of TRPV1 single channel activity under perfusion with saline solution.

FIG. 10, Panel A shows a sample record of TRPV1 single channel activity under perfusion with saline solution, while Panel B shows sample recording of single-channel activity from cells incubated in HA and recorded under perfusion with HA solution. The insets represent single channel amplitude probability histograms of patches recorded under saline (black) and after exposure to HA (gray). FIG. 10, Panel C shows I-V curves obtained in control conditions (squares) and after exposure to HA (circles), while Panel D shows single channel amplitudes obtained from individual patches, represented as squares (control) and circles (HA-treated). Larger symbols correspond to the data from the measures performed in the traces shown in Panels A and B. The bars correspond to the mean values of single channel amplitudes±s.e.m in each condition; t-test, P=0.73 N.S.

FIG. 10, Panel E shows the probability of the open state for different patches. Larger symbols represent the data from the measurements performed in the traces shown in Panels A and B. The bars represent mean values of single-channel open probability±s.e.m; t-student, **P=0.002. Notably, long closing states that were very infrequent in control conditions increased in their frequency after treatment with HA. No differences could be observed in the incidence of open states between HA-treated and control conditions.

The results shown in FIG. 10 demonstrate that in the presence of HA, TRPV1 channel activity in response to capsaicin is absent in about 30% of the patches. Moreover, the probability of occurrence of open states is dramatically reduced in the presence of HA. The single-channel I-V relationship and single-channel current amplitude in control conditions and in the presence of HA were similar. However, HA caused an increase in the number of long-duration events in the closed-time histograms, as is evidenced by the measurements of the distribution of channel open and closed times. Accordingly, the results suggest that HA maintains the channel closed for longer times, thus reducing its probability of opening. The consequence is that nociceptive neurons become less excitable by noxious stimuli that open TRPV1 channels in the presence of HA.

Figure 11:
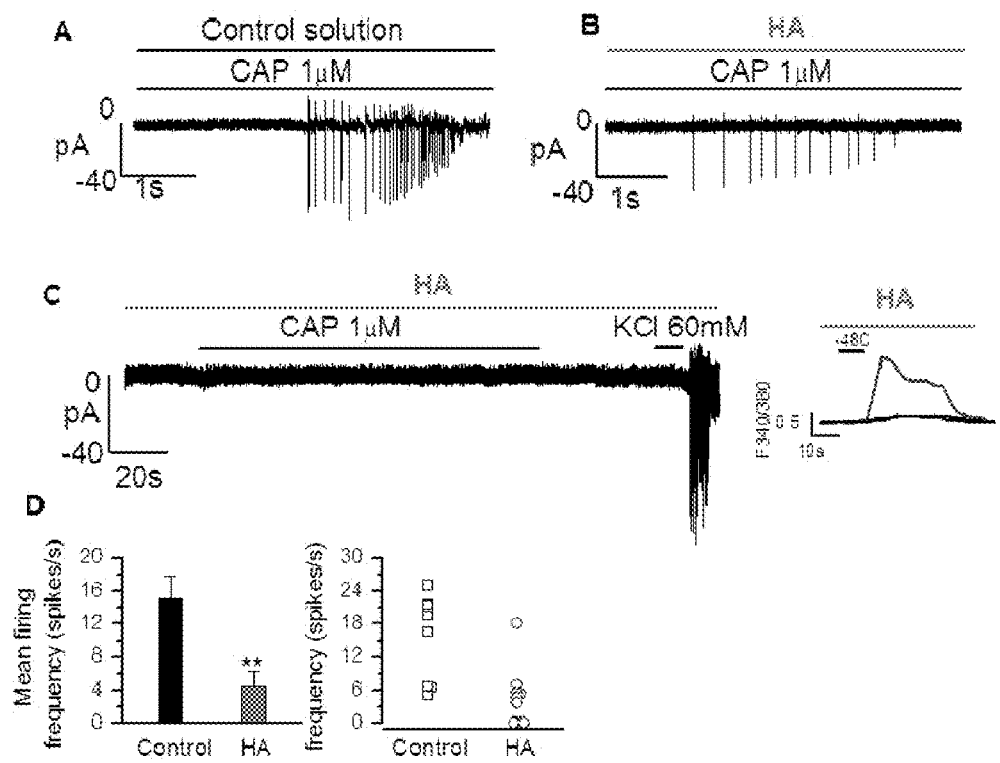
FIG. 11, Panel A shows a sample record of the response to capsaicin in a single DRG neuron perfused with saline solution.

In nociceptive DRG neurons possessing TRPV1 channels the opening of these channels by capsaicin causes a decrease in input resistance, depolarization and action potential firing. The firing frequency of action potentials evoked by 1 μM capsaicin was measured with patch-clamps in dissociated DRG neurons that express TRPV1. Specifically, electrophysiological recordings of DRG neurons were performed in the cell-attached configuration at −60 mV holding potential in the presence of 1 μM capsaicin. FIG. 11, Panel A shows a sample record of the response to capsaicin in a single DRG neuron perfused with saline solution. Mean firing frequency of the response was 16 spikes/second. FIG. 11, Panel B shows a sample record of capsaicin stimulation in a DRG neuron treated with HA and recorded in the presence of HA. Mean frequency of the response was 4.6 spikes/second. FIG. 11, Panel C shows a sample record of a DRG neuron treated with HA and recorded in HA, in which no response to capsaicin was observed but impulse discharge could be evoked with 60 mM KCl. The inset shows elevation in intracellular calcium produced by a heat pulse in this neuron. Absence of intracellular calcium rise to the same heat pulse in two different neurons is apparent in the bottom trace.

FIG. 11, Panel D shows mean firing frequency (left) and individual data (right) of DRG neurons under control conditions (left bar, n=8), and after exposure to HA (right bar, n=9).

The results presented in FIG. 11 demonstrate that in the presence of HA, 4 out of 10 neurons that had previously responded to capsaicin did not fire action potentials, despite their intact excitability to other stimuli. The average firing frequency evoked by capsaicin in control DRG neurons was significantly reduced in DRG neurons incubated with HA. Finally, sensitization of TRPV1 channels of DRG neurons by the inflammatory mediator bradykinin was significantly reduced by HA. Altogether, these results indicate that in DRG neurons, HA selectively inhibits the impulse firing evoked by capsaicin, modulating the function of TRPV1 through direct or indirect interaction with the channel.

Example 5

Direct Inhibition of Nerve Impulse Activity by the HA Compositions of the Invention In another group of experiments, the latency of the first nocifensive response was measured in wild-type (WT) or TRPV1−/− knockout (KO) mice after subjecting them to the Hot Plate Test. The latency of the first nocifensive response (licking, biting, lifting, guarding, shaking the hind paw or jumping), is considered a behavioral expression of the acute pain evoked by the noxious heat stimulus acting on the paws. The latency value was measured and compared between control animals (baseline), animals that received in the paw a subcutaneous injection of 10 μl of sterile saline solution, of 400 μg/ml HA or of hyaluronidase, the enzyme digesting the native hyaluronic acid surrounding the extracellular matrix around pain nerve terminals.

Figure 12:
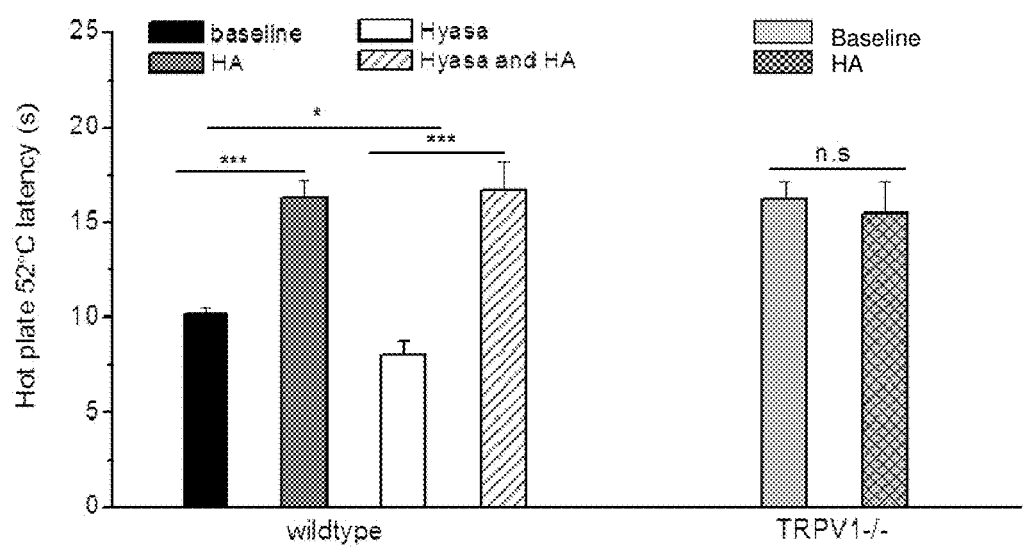
FIG. 12, shows the latency of the nociceptive response of mice in the hot plate test to a plate temperature of 52° C. in wild type (left panel) and in TRPV1 knock-out mice (right panel), after subcutaneous injection in the paw of 10 μl of sterile saline, HA, hyaluronidase (Hyasa 6U) or hyaluronidase followed by another injection of HA.

As shown in FIG. 12, the latency of the nocifensive response to the 52° C. heat was significantly reduced by hyaluronidase 7 days later, whereas HA increased the latency, reflecting a reduced sensitivity to noxious heat. The maximal analgesic effects of HA injection were seen 48 hours after its injection. In an additional group of animals, HA was injected days after the hyaluronidase injection, to replace native hyaluronic acid destroyed by the enzyme. In these conditions, latency recovered normal values. This data suggests that the HA inhibits TRPV1, thus reducing the TRPV1-mediated sensitivity of the nociceptor endings to noxious stimuli. When the experiments were repeated in genetically-modified TRPV1$^{-/-}$ mice, none of the differences in the hot-plate test responses between treatments seen in wild type animals were observed.

To confirm that the inhibition of TRPV1 channels by HA also occurred in the TRPV1 channels of the pain fibers of the knee joints that are activated by joint rotation (FIG. 13A), 10 μM capsaicin was injected intra-arterially in anesthetized rats as a bolus through a catheter into the saphenous artery close to the knee joint at regular 30 minute intervals before and after intra-articular injection of saline or HA. The impulse activity evoked by close intra-arterial injection of 10 μM capsaicin and responses to controlled rotation of the knee joint were measured (see FIG. 13.

Figure 13:
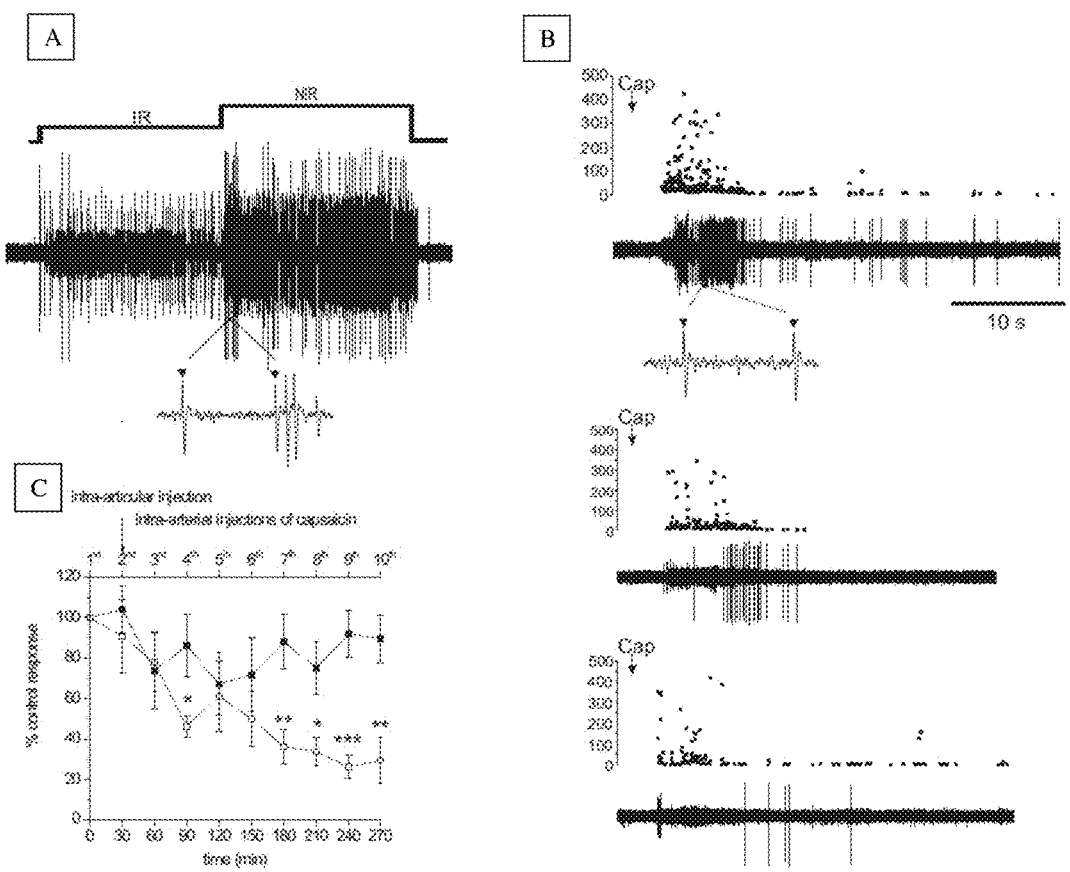
FIG. 13, Panel A shows the nerve impulse activity evoked by a joint movement in an anesthetized rat.

The bolus injection of capsaicin elicited a discharge of nerve impulses in a part of the explored filaments (FIG. 13, Panel B). The number of impulses evoked by the first injection (control response) was taken as 100% and served to express the amplitude of the response to the following injections. The impulse firing frequency was always reduced after the second or third stimulus, persisting throughout the complete injection series (tachyphylaxis) decreasing on the average to 88±13 (n=7) of the control response in 180 min when intra-articular saline was injected (FIG. 13, Panel B, black squares). When 4% HA was injected, the percent reduction of the discharge was 31±7 (n=6) which represents a 65% of reduction. This inhibitory effect was higher at the end of the experiment, 270 min after intra-articular injection of HA, when 84% of activity reduction was observed (FIG. 13, Panel B, open squares). Collectively, these findings confirm that HA inhibits directly TRPV1 channels in pain nerve fibers of the knee joint.

Example 6

Force Requirements for Ejection of HA Through Various Needle Sizes

Figure 14:
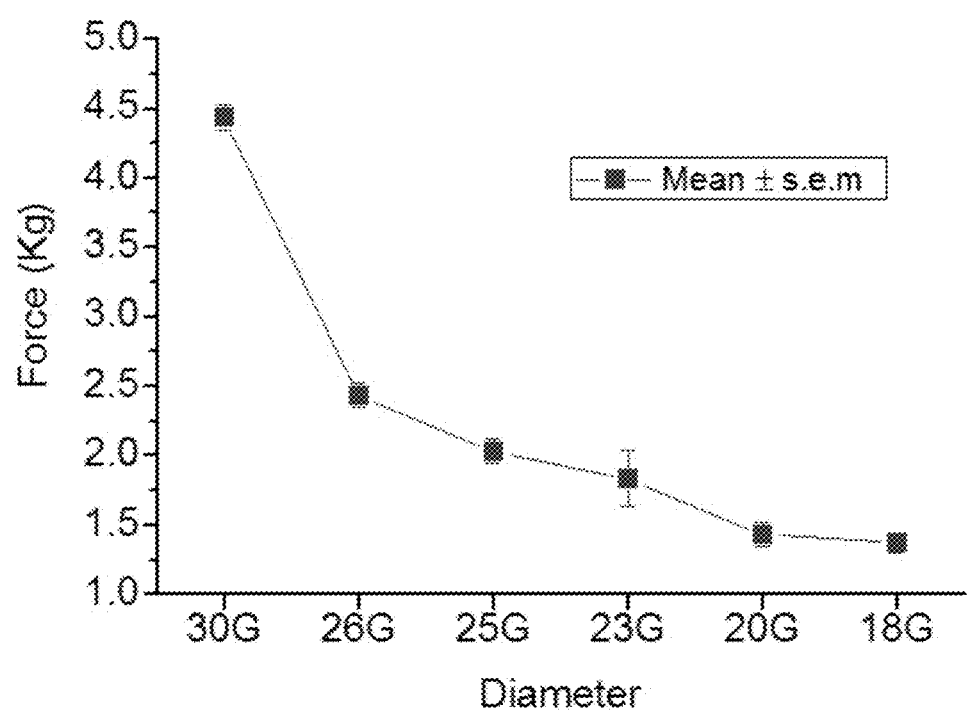
FIG. 14 shows the pressure required to eject a 4% HA solution through needles of different sizes.

The pressure required to eject a 4% HA composition from a 3 ml syringe with needles of different diameter (30-18G) has been measured and is shown in FIG. 14. Force was exerted by one plate of a two-plate balance, acting perpendicularly on the embolus of the syringe. Weights of increasing magnitude were added to the contralateral plate. As demonstrated by the results shown in FIG. 14, the HA compositions of the invention can be administered to subjects using needles with diameters of 30-18G.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method of inhibiting activation of an ion channel involved in pain transduction in a subject in need thereof, the method comprising administering to the subject a high elasticity composition comprising hyaluronan, wherein:
the hyaluronan is not cross-linked and/or is substantially free of chemical modifications;
wherein the composition is substantially free of a pharmaceutically active substance selected from the group consisting of a protein, a glycosaminoglycan that is different from hyaluronan, hydroxypropyl methyl cellulose and a local anesthetic; and
wherein the composition has an elasticity (G') of at least about 900 Pascal when measured at a frequency of 5.0 Hz, thereby inhibiting activation of the ion channel involved in pain transduction in the subject.

2. The method of claim 1, wherein hyaluronan is present in the high elasticity composition at a concentration of greater than 30 mg/mL.

3. The method of claim 2, wherein hyaluronan is present in the high elasticity composition at a concentration of 40 mg/mL to 60 mg/mL.

4. The method of claim 1, wherein the hyaluronan has an average molecular weight of between 1 million and 2 million.

5. The method of claim 1, wherein the hyaluronan has an average molecular weight of less than 2 million.

6. The method of claim 1, wherein the high elasticity composition is sterile.

7. The method of claim 1, wherein the high elasticity composition further comprises a buffer.

8. The method of claim 7, wherein the buffer is phosphate buffered saline (PBS).

9. The method of claim 8, wherein the buffer comprises NaCl, $NaH_2PO_4 \cdot H_2O$, and $Na_2HPO_4$.

10. The method of claim 9, wherein the buffer comprises 8.47 g/L NaCl, 0.047 g/L $NaH_2PO_4 H_2O$ and 0.213 g/L $Na_2HPO_4$.

11. The method of claim 1, wherein the ion channel involved in pain transduction is a TRPV1 ion channel.

12. The method of claim 1, wherein administering the high elasticity composition results in inhibition of an increase in cytosolic $Ca^{2+}$ following a nociceptive stimulus in a neuron expressing the ion channel involved in pain transduction.

13. The method of claim 1, wherein administering the high elasticity composition results in a decrease in a whole-cell current following a nociceptive stimulus in a neuron expressing the ion channel involved in pain transduction.

14. A method of treating pain in a subject in need thereof, the method comprising administering to the subject a high elasticity composition comprising hyaluronan, wherein:
the hyaluronan is not cross-linked and/or is substantially free of chemical modifications;
wherein the composition is substantially free of a pharmaceutically active substance selected from the group consisting of a protein, a glycosaminoglycan that is different from hyaluronan, hydroxypropyl methyl cellulose and a local anesthetic; and
wherein the composition has an elasticity (G') of at least about 900 Pascal when measured at a frequency of 5.0 Hz, thereby treating pain in the subject.

15. The method of claim 14, wherein hyaluronan is present in the high elasticity composition at a concentration of greater than 30 mg/mL.

16. The method of claim 15, wherein hyaluronan is present in the high elasticity composition at a concentration of 40 mg/mL to 60 mg/mL.

17. The method of claim 14, wherein the hyaluronan has an average molecular weight of between 1 million and 2 million.

18. The method of claim 14, wherein the hyaluronan has an average molecular weight of less than 2 million.

19. The method of claim 14, wherein the high elasticity composition is sterile.

20. The method of claim 14, wherein the high elasticity composition further comprises a buffer.

21. The method of claim 20, wherein the buffer is phosphate buffered saline (PBS).

22. The method of claim 21, wherein the buffer comprises NaCl, $NaH_2PO_4 \cdot H_2O$, and $Na_2HPO_4$.

23. The method of claim 22, wherein the buffer comprises 8.47 g/L NaCl, 0.047 g/L $NaH_2PO_4 \cdot H_2O$ and 0.213 g/L $Na_2HPO_4$.

24. The method of claim 14, wherein administering the high elasticity composition results in a decrease in a mean number of pain nerve impulses in the subject.

25. The method of claim 1, wherein the ion channel involved in pain transduction is in a nerve of a joint of the subject.

26. The method of claim 25, wherein the joint is selected from the group consisting of a knee joint, an elbow joint, a hip joint and a shoulder joint.

27. The method of claim 14, wherein the pain is in a joint of the subject.

28. The method of claim 27, wherein the joint is selected from the group consisting of a knee joint, an elbow joint, a hip joint and a shoulder joint.

* * * * *